United States Patent
Alonso et al.

(10) Patent No.: US 8,188,282 B2
(45) Date of Patent: May 29, 2012

(54) REGIOSELECTIVE PALLADIUM CATALYZED SYNTHESIS OF BENZIMIDAZOLES AND AZABENZIMIDAZOLES

(75) Inventors: Jorge Alonso, Mannheim (DE); Andreas Lindenschmidt, Frankfurt (DE); Marc Nazare, Frankfurt (DE); Nis Halland, Frankfurt (DE); Omar Rkyek, Frankfurt (DE); Matthias Urmann, Frankfurt (DE)

(73) Assignee: Sanofi-Aventis, Paris (FR)

( * ) Notice: Subject to any disclaimer, the term of this patent is extended or adjusted under 35 U.S.C. 154(b) by 586 days.

(21) Appl. No.: 12/353,271

(22) Filed: Jan. 14, 2009

(65) Prior Publication Data
US 2009/0203912 A1 Aug. 13, 2009

Related U.S. Application Data

(63) Continuation of application No. PCT/EP2007/005816, filed on Jun. 30, 2007.

(30) Foreign Application Priority Data

Jul. 15, 2006 (EP) ..................... 06014789

(51) Int. Cl.
*C07D 513/02* (2006.01)
*C07D 235/00* (2006.01)
(52) U.S. Cl. ..................... 546/118; 548/304.4
(58) Field of Classification Search ................ 546/118; 548/304.4
See application file for complete search history.

(56) References Cited

U.S. PATENT DOCUMENTS
6,124,323 A 9/2000 Bigge et al.
2005/0203078 A1 9/2005 Priepke et al.

FOREIGN PATENT DOCUMENTS
WO WO 2006/069807 A1 7/2006

OTHER PUBLICATIONS

Yin et al, Palladium-Catalyzed Intermolecular Coupling of Aryl Halides and Amides, Organic Letters, 2000 (2) 8, pp. 1101-1104.
Beaulieu, A Practical Oxone—Mediated, High-Throughput, Solution-Phase Synthesis of Benzimidazoles from 1,2-Penylenediamines and Aldehydes and its Application to Preparative Scale Synthesis, Synthesis 2003 (11) pp. 1683-1692.
Browning et al, Palladium-catalyzed aryl-amidation. Synthesis of non-racemic N-aryl lactams, Tetrahedron, 2004 (60), pp. 359-365.
Caddick, Microwave Assisted Organic Reactions, Tetrahedron 1995 (51) 38 pp. 10403-10432.
Hauel et al, Structure-Based Design of Novel Potent Nonpeptide Thrombin Inhibitors, J. Med. Chem. 2002 (45) pp. 1757-1766.
Horton et al, The Combinatorial Synthesis of Bicyclic Privileged Structures or Privileged Substructures, Chem. Rev. 2003 (103) pp. 893-930.
Katritzky et al, New Routes to Selectively Methylated Benzimidazoles, J. Heterocyclic Chem. 1994 (31) pp. 775-779.
Krstenansky, et al., Recent Advances in Microwave-assisted Organic Synthesis, Current Opinion in Drug Discovery & Development; 3(4); 2000; pp. 454-461.
Larhed, et al., Microwave-assisted high-speed chemistry: a new technique in drug discovery, Drug Discovery Today; 8; 2001; pp. 406-416.
Lidstrom, et al., Microwave assisted organic synthesis—a review, Tetrahedron; 57; 2001; pp. 9225-9283.
Wienen et al, A Review on Telmisartan: A Novel, Long-Acting AngiotensisII-Receptor Antagonist, Cardiovascular Drug Reviews 2000 (18) 2 pp. 127-154.
Yang et al, A Versatile Method for the Synthesis of Benzimidazoles from o-Nitroanilines and Aldehydes in One Step via a Reductive Cyclization, Synthesis 2005 (1) pp. 47-56.

*Primary Examiner* — Nizal Chandrakumar
(74) *Attorney, Agent, or Firm* — Scully, Scott, Murphy & Presser, P.C.

(57) ABSTRACT

The present invention relates to a process for the regioselective synthesis of compounds of the formula I,

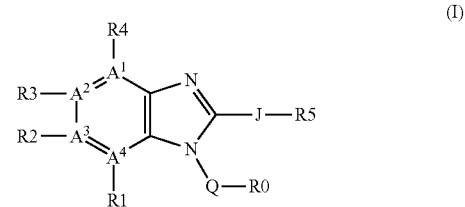

wherein R0; R1; R2; R3; R4; R5; A1; A2; A3; A4, Q and J have the meanings indicated in the claims. The present invention provides a direct palladium catalyzed, regioselective process to a wide variety of unsymmetrical, multifunctional N-substituted benzimidazoles or azabenzimidazoles of formula I starting from 2-halo-nitroarenes and N-substituted amides useful for the production of pharmaceuticals, diagnostic agents, liquid crystals, polymers, herbicides, fungicidals, nematicidals, parasiticides, insecticides, acaricides and arthropodicides.

20 Claims, No Drawings

REGIOSELECTIVE PALLADIUM CATALYZED SYNTHESIS OF BENZIMIDAZOLES AND AZABENZIMIDAZOLES

FIELD OF THE INVENTION

The present invention relates to a process for the regioselective synthesis of compounds of the formula (I),

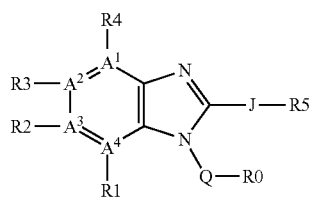

in which R0; R1; R2; R3; R4; R5; A1; A2; A3; A4, Q and J have the meanings indicated below that are useful as intermediates for the preparation of valuable pharmaceutically active ingredients.

BACKGROUND OF THE INVENTION

The present invention relates to a direct palladium catalyzed, regioselective process for the preparation of a wide variety of unsymmetrical, multifunctional N-substituted benzimidazoles or azabenzimidazoles of the formula (I) starting from 2-halo-nitroarenes and N-substituted amides.

Benzimidazoles play an important role in drug discovery and can certainly be regarded as privileged structures in pharmaceutical research (D. A. Horton, G. T. Bourne, M. L. Smythe, Chem. Rev. 2003, 103, 893-930). The ability of this benzimidazole scaffold to mediate an interaction with a variety of biological targets, is well-documented by the multitude of reports on the observed biological activity, as well as by the fact that several benzimidazole- or azabenzimidazole-based compounds are in development or marketed as drugs and make this type of heterocycle a important element for a valuable pharmaceutically active ingredient. (W. Wienen, M. Entzeroth, J. C. A. Van Meel, J. Stangier, U. Busch, T. Ebner, J. Schmid, H. Lehmann, K. Matzek, J. Kempthorne-Rawson, V. Gladigau, N. H. Hauel, *Cardiovascular Drug Rev.* 2000, 18, 127-156; N. H. Hauel, H. Nar, H. Priepke, U. Ries, J-M. Stassen, W. Wienen, *J. Med. Chem.* 2002, 45, 1757-1766.)

Of course the use of benzimidazoles or azabenzimidazoles is not limited to the above-mentioned pharmaceutical application. For example it is well known that benzimidazoles or azabenzimidazoles can be useful in agricultural applications like for example as herbicides, fungicides, nematicidals, parasiticides, insecticides, acaricides and arthropodicides or as diagnostic agents, liquid crystals and as polymers. In several cases, the benzimidazole or azabenzimidazoles is unsymmetrical and selectively substituted at one of the nitrogen atoms of the imidazole moiety. In contrast to the great importance of this scaffold no general regioselective route to N-substituted benzimidazoles or azabenzimidazoles has been described yet. The few methods available so far are multi-step processes often requiring harsh reaction conditions and are restricted in the substrate range, have poor cost-effectiveness and are thus of limited use (P. N. Preston, in *The Chemistry of Heterocyclic Compounds, Vol.* 40 (Eds.: A. Weissberger, E. C. Taylor), John Wiley & Sons, New York, 1981. P. L. Beaulieu, B. Haché, E. von Moos, *Synthesis* 2003, 1683-1692. D. Yang, D. Fokas, J. Li, L. Yu, C. M. Baldino, *Synthesis* 2005, 47-56; Y. M. Yutilov, *Adv. Heterocycl. Chem.* 2005, 89, 159-270). Furthermore, it is surprising that palladium-catalyzed reactions have hardly been used for the regioselective construction of an N-substituted benzimidazole scaffold and if so, the mentioned shortcomings were not eliminated (Katritzky, A. R.; Rachwal, S.; Ollmann, R.; *J Heterocycl. Chem.* 1994, 31, 775-779). Although palladium-catalyzed protocols for the cross-coupling between aryl halides and amides have been reported, very few examples employing 2-halo-nitroarenes exist. J. Yin, S. L. Buchwald describe in one example the coupling of 2-bromo-1-methyl-3-nitro-benzene with acetamide (*Org. Lett.* 2000, 2, 1101-1104) and R. G. Browning, V. Badarinarayana, H. Mahmud, C. J. Lovely, describe in one example the coupling of 1-bromo-2-nitro-benzene and a pyrrolidin-2-one derivative in moderate yield (*Tetrahedron* 2004, 60, 359-365). However, no general applicability for the palladium-catalyzed cross-coupling of 2-halo-nitroarenes, in particular 2-chloro-nitroarenes, and N-substituted amides was shown, and in addition no use was made to for the regioselective synthesis of benzimidazoles or azabenzimidazoles.

The limited regioselective access to N-substituted benzimidazoles or azabenzimidazoles often prevents the optimization of a potential drug substance or substance with for example agricultural application and is accompanied by poor cost-effectiveness. Thus the present invention is useful in preparing intermediates or end products of biological active compounds in pharmaceutical and agricultural applications.

SUMMARY OF THE INVENTION

The present invention provides a direct palladium catalyzed, regioselective synthetic route to a wide variety of unsymmetrical, multifunctional N-substituted benzimidazoles or azabenzimidazoles of formula I starting from 2-halo-nitroarenes of formula II and substituted amides of formula III. Thus one aspect of the invention is an efficient and general palladium catalyzed coupling method for substituted 2-halo-nitroarenes (step 1) to intermediates of formula IV. In another aspect of the invention, an efficient process is provided for the subsequent reductive aminocyclization (step 2) of intermediates of formula IV, which can be either performed with the crude reaction mixture of step 1 or optionally after simple filtration through a pad of Celite by using a reducing reagent.

The advantages of the provided process are that it comprises a novel, direct regioselective catalytic, mild and general method for the synthesis of N-substituted benzimidazoles or azabenzimidazoles, which also can be performed as a one-pot procedure. Thus, the process is very time- and cost-effective. Moreover, are the reaction conditions compatible with a broad range of functional groups and a large variety of starting materials, which are easily accessible or even commercially available.

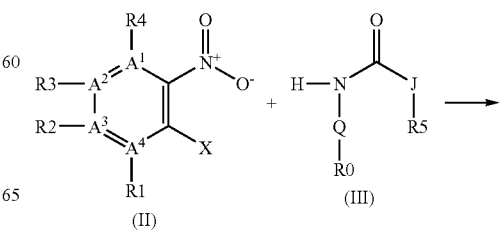

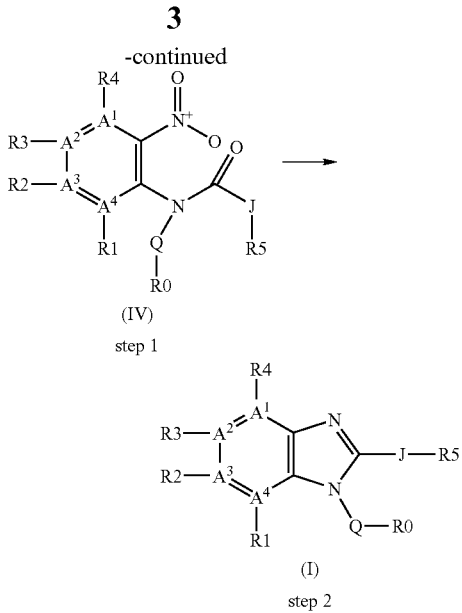

(IV)

step 1

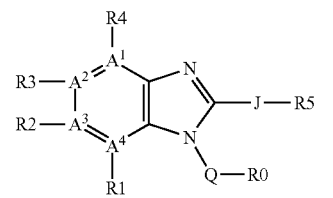

(I)

step 2

DETAILED DESCRIPTION OF THE INVENTION

A process for preparing a compound of formula I

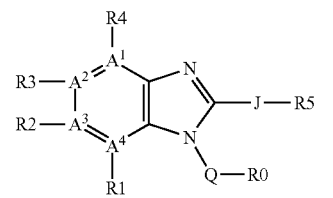
(I)

and/or all stereoisomeric forms of the compound of formula I, and/or mixtures of these forms in any ratio, and/or a physiologically tolerated salt of the compound of formula I, wherein A1, A2, A3, A4 are independently from each other selected from carbon or nitrogen atoms to form together with the two carbon atoms in formula I a stable aromatic or heteroaromatic ring;

Q is —$(C_1-C_6)$-alkylene, wherein alkylene is unsubstituted or mono-, di- or trisubstituted independently of one another by R14; or
—$(C_3-C_8)$-cycloalkyl, wherein cycloalkyl is unsubstituted or mono-, di- or trisubstituted independently of one another by R14; or
—$(C_6-C_{14})$-aryl, wherein aryl is unsubstituted or mono-, di-, tri- or four times substituted independently of one another by R13; or
—$(C_4-C_{14})$-heteroaryl, wherein heteroaryl is unsubstituted or mono-, di-, tri- or four times substituted independently of one another by R13;

J is —$(C_1-C_6)$-alkylene, wherein alkylene is unsubstituted or mono-, di- or trisubstituted independently of one another by R14; or
—$(C_3-C_8)$-cycloalkyl, wherein cycloalkyl is unsubstituted or mono-, di- or trisubstituted independently of one another by R14; or
—$(C_6-C_{14})$-aryl, wherein aryl is unsubstituted or mono-, di-, tri- or four times substituted independently of one another by R13; or
—$(C_4-C_{14})$-heteroaryl, wherein heteroaryl is unsubstituted or mono-, di-, tri- or four times substituted independently of one another by R13;

R0, R1, R2, R3, R4 and R5 are independent of one another identical or different and are
a) hydrogen atom,
b) —$(C_1-C_4)$-alkyl, wherein alkyl is unsubstituted or substituted one to three times by R13,
c) halogen,
d) phenyloxy-, wherein phenyloxy is unsubstituted or substituted one to three times by R13,
e) —$(C_1-C_3)$-fluoroalkyl,
f) —N(R10)-$(C_1-C_4)$-alkyl, wherein alkyl is unsubstituted or substituted one to three times by R13,
g) —$(C_6-C_{14})$-aryl, wherein aryl is unsubstituted or mono-, di-, tri- or four times substituted independently of one another by R13,
h) —$(C_4-C_{14})$-heteroaryl, wherein heteroaryl is unsubstituted or mono-, di-, tri- or four times substituted independently of one another by R13,
i) —$(C_3-C_8)$-cycloalkyl, wherein said cycloalkyl is unsubstituted or mono-, di-, tri- or four times substituted independently of one another by R13, or
j) a 3- to 7-membered cyclic residue, containing up to 1, 2, 3 or 4 heteroatoms chosen from nitrogen, sulfur or oxygen, wherein said cyclic residue is unsubstituted or mono-, di-, tri- or four times substituted independently of one another by R13,
k) —O—$CF_3$,
l) —O—$(C_1-C_4)$-alkyl, wherein alkyl is unsubstituted or substituted one to three times by R13,
m) —$NO_2$,
n) —CN,
o) —OH,
p) —C(O)—R10,
q) —C(O)—O—R11,
r) —C(O)—N(R11)-R12,
s) —N(R11)-R12,
t) —N(R10)-$SO_2$—R10,
v) —S—R10,
w) —$SO_n$—R10, wherein n is 1 or 2,
x) —$SO_2$—N(R11)-R12 or
y) at least one of R1, R2, R3 or R4 are absent in case one or more of A1, A2, A3 or A4 are nitrogen atom, R1 and R2, R2 and R3 or R3 and R4 form together with the atoms which they are attached to a 5- or 8-membered ring, containing 0, 1, 2, 3 or 4 heteroatoms chosen from nitrogen, sulfur or oxygen, wherein said ring is unsubstituted or substituted one, two, three or four times by R14, R10 is hydrogen atom, —$(C_1-C_3)$-fluoroalkyl or —$(C_1-C_6)$-alkyl, R11 and R12 are independently of one another identical or different and are
a) hydrogen atom,
b) —$(C_1-C_6)$-alkyl, wherein alkyl is unsubstituted or mono-, di- or trisubstituted independently of one another by R13,
c) —$(C_6-C_{14})$-aryl-, wherein aryl is unsubstituted or mono-, di- or trisubstituted independently of one another by R13,
d) —$(C_4-C_{14})$-heteroaryl, wherein heteroaryl is unsubstituted or mono-, di- or trisubstituted independently of one another by R13 or R13 is halogen, —$NO_2$, —CN, =O, —OH, —$(C_1-C_8)$-alkyl, —$(C_1-C_8)$-alkoxy, —$CF_3$, phenyloxy-, —C(O)—R10, —C(O)—O—R17, —C(O)—N—(R17)-R18, —N(R17)-R18, —N(R10)-$SO_2$—R10, —S—R10, —$SO_n$—R10, wherein n is 1 or 2, —SO$_2$—N(R17)-R18, —(C$_6$-C$_{14}$)-aryl, wherein aryl is unsubstituted or mono-, di- or trisubstituted independently of one another by R14, —(C$_4$-C$_{14}$)-heteroaryl, wherein heteroaryl is unsubstituted or mono-, di- or trisubstituted independently of one another by R14, —(C$_3$-C$_8$)-cycloalkyl, wherein said cycloalkyl is unsubstituted or mono-, di- or trisubstituted independently of one another by R14, or a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, R14 is halogen, —OH, =O, —CN, —CF$_3$, —(C$_1$-C$_8$)-alkyl, —(C$_1$-C$_4$)-alkoxy, —NO$_2$, —C(O)—OH, —NH$_2$, —C(O)—O—(C$_1$-C$_4$)-alkyl, —(C$_1$-C$_8$)-alkylsulfonyl, —C(O)—NH—(C$_1$-C$_8$)-alkyl, —C(O)—N—[(C$_1$-C$_8$)-alkyl]$_2$, —C(O)—NH$_2$, —S—R10, —N(R10)-C(O)—NH—(C$_1$-C$_8$)-alkyl, or —N(R10)-C(O)—N—[(C$_1$-C$_8$)-alkyl]$_2$, R17 and R18 are independently of one another identical or different and are
a) hydrogen atom,
b) —(C$_1$-C$_6$)-alkyl,
c) —(C$_6$-C$_{14}$)-aryl- or
d) —(C$_4$-C$_{14}$)-heteroaryl, said process comprises a reaction of a compound of formula II

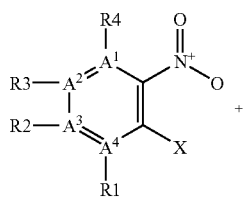

(II)

wherein R1, R2, R3, R4, A1, A2, A3 and A4 are as defined in formula I and X is Cl, Br, I, triflate or nonaflate, with a compound of formula III

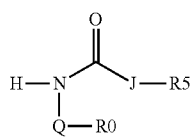

(III)

wherein Q, J, R0 and R5 are as defined in formula I,
in the presence of a palladium catalyst, a base, a ligand and an aprotic solvent to give a compound of formula IV

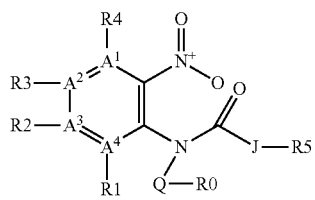

(IV)

and converting the compound of formula IV into a compound of formula I in the presence of a reducing reagent and a second solvent and optionally the compound of formula I is converted to its physiologically tolerated salt. The present invention also relates to a process for the preparation of a compound of formula I, wherein A1, A2, A3 and A4 together with the two carbon atoms in formula I form a benzene, pyrazine, pyridazine, pyridine, pyrimidine, triazine or tetrazine, Q is —(C$_1$-C$_6$)-alkylene, wherein alkylene is unsubstituted or mono-, di- or trisubstituted independently of one another by R14;
—(C$_3$-C$_6$)-cycloalkyl, wherein cycloalkyl is unsubstituted or mono-, di- or trisubstituted independently of one another by R14;
phenyl, wherein phenyl is unsubstituted or mono-, di-, tri- or four times substituted independently of one another by R13; or
—(C$_4$-C$_{14}$)-heteroaryl, wherein heteroaryl is selected from acridinyl, azaindole (1H-pyrrolopyridinyl), azabenzimidazolyl, azaspirodecanyl, azepinyl, azetidinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketoperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein heteroaryl is unsubstituted or mono-, di-, tri- or four times substituted independently of one another by R13;

J is a covalent bond,
—(C$_1$-C$_6$)-alkylene, wherein alkylene is unsubstituted or mono-, di- or trisubstituted independently of one another by R14;

—($C_3$-$C_6$)-cycloalkyl, wherein cycloalkyl is unsubstituted or mono-, di- or trisubstituted independently of one another by R14;

phenyl, wherein phenyl is unsubstituted or mono-, di-, tri- or four times substituted independently of one another by R13; or —($C_4$-$C_{14}$)-heteroaryl, wherein heteroaryl is as defined above and is unsubstituted or mono-, di-, tri- or four times substituted independently of one another by R13;

R0, R1, R2, R3, R4 and R5 are independent of one another identical or different and are a) hydrogen atom,
b) F,
c) Cl or Br,
d) —($C_1$-$C_4$)-alkyl, wherein alkyl is unsubstituted or substituted one to three times by R13,
e) —($C_1$-$C_3$)-fluoroalkyl,
f) phenyl, wherein phenyl is unsubstituted or substituted one to three times by R13,
g) —($C_4$-$C_{14}$)-heteroaryl, wherein heteroaryl is as defined above and is unsubstituted or mono-, di-, tri- or four times substituted independently of one another by R13,
h) —($C_3$-$C_8$)-cycloalkyl, wherein said cycloalkyl is unsubstituted or mono-, di-, tri- or four times substituted independently of one another by R13,
i) a 3- to 7-membered cyclic residue selected from azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazol e, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, and is unsubstituted or mono-, di-, tri- or four times substituted independently of one another by R13,
j) —O—$CF_3$,
k) —O—($C_1$-$C_4$)-alkyl, wherein alkyl is unsubstituted or substituted one to three times by R13,
l) —N(R10)-($C_1$-$C_4$)-alkyl, wherein alkyl is unsubstituted or substituted one to three times by R13,
m) —CN,
n) —OH,
o) phenyloxy-, wherein phenyloxy is unsubstituted or substituted one to three times by R13,
p) —C(O)—O—R11,
q) —C(O)—N(R11)-R12,
r) —N(R11)-R12,
s) —N(R10)-$SO_2$—R10,
t) —S—R0,
v) —$SO_n$—R10, wherein n is 1 or 2,
w) —$SO_2$—N(R11)-R12,
x) —C(O)—R10 or
y) at least one of R1, R2, R3 or R4 are absent in case one or more of A1, A2, A3 or A4 are nitrogen atom, R10 is hydrogen atom, —($C_1$-$C_3$)-fluoroalkyl or —($C_1$-$C_6$)-alkyl, R11 and R12 are independently of one another identical or different and are a) hydrogen atom,
b) —($C_1$-$C_4$)-alkyl, wherein alkyl is unsubstituted or mono-, di- or trisubstituted independently of one another by R13,
c) phenyl, wherein phenyl is unsubstituted or mono-, di- or trisubstituted independently of one another by R13,
d) —($C_4$-$C_{14}$)-heteroaryl, wherein heteroaryl is as defined above and is unsubstituted or mono-, di- or trisubstituted independently of one another by R13 or R13 is F, Cl, —CN, =O, —OH, —($C_1$-$C_8$)-alkyl, —($C_1$-$C_8$)-alkoxy, —$CF_3$, phenyloxy-, —C(O)—R10, —C(O)—O—R17, —C(O)—N—(R17)-R18, —N(R17)-R18, —N(R10)-$SO_2$—R10, —S—R10, —$SO_n$—R10, wherein n is 1 or 2, —$SO_2$—N(R17)-R18, phenyl, wherein phenyl is unsubstituted or mono-, di- or trisubstituted independently of one another by R14, —($C_4$-$C_{14}$)-heteroaryl, wherein heteroaryl is as defined above is unsubstituted or mono-, di- or trisubstituted independently of one another by R14, —($C_3$-$C_6$)-cycloalkyl, wherein said cycloalkyl is unsubstituted or mono-, di- or trisubstituted independently of one another by R14, or a 3- to 7-membered cyclic residue, which is as defined above and is unsubstituted or mono-, di- or trisubstituted independently of one another by R14, R14 is F, Cl, —OH, =O, —CN, —$CF_3$, —($C_1$-$C_8$)-alkyl, —($C_1$-$C_4$)-alkoxy, —C(O)—OH, —$NH_2$, —C(O)—O—($C_1$-$C_4$)-alkyl, —($C_1$-$C_8$)-alkylsulfonyl, —C(O)—$NH_2$, —S—R10, —C(O)—NH—($C_1$-$C_8$)-alkyl, —C(O)—N—[($C_1$-$C_8$)-alkyl]$_2$, —N(R10)-C(O)—NH—($C_1$-$C_8$)-alkyl or —N(R10)-C(O)—N[($C_1$-$C_8$)-alkyl]$_2$, R17 and R18 are independently of one another identical or different and are a) hydrogen atom,
b) —($C_1$-$C_4$)-alkyl,
c) phenyl or
d) —($C_4$-$C_{14}$)-heteroaryl and X is Cl, Br or I.

The present invention also relates to a process for the preparation of a compound of formula I, wherein A1, A2, A3 and A4 together with the two carbon atoms in formula I form a benzene or pyridine, Q is phenyl, which is unsubstituted or substituted by R13, —($C_1$-$C_6$)-alkylene or pyridyl, R0, R1, R2, R3, R4 and R5 are independent of one another identical or different and are a) hydrogen atom,
b) F,
c) Cl,
d) Br,
e) —($C_1$-$C_4$)-alkyl,
f) —($C_3$-$C_6$)-cycloalkyl
g) phenyl,
h) —O—($C_1$-$C_4$)-alkyl,
i) —C(O)—O—R1,
j) —CN,
k) —C(O)—R10 or
l) at least one of R1, R2, R3 or R4 are absent in case one or more of A1, A2, A3 or A4 are nitrogen atom, R10 is hydrogen atom or —($C_1$-$C_4$)-alkyl,
R11 is hydrogen atom or —($C_1$-$C_4$)-alkyl,
R13 is —C(O)—O—R17,
R14 is Cl, F, —($C_1$-$C_8$)-alkyl or —C(O)—O—($C_1$-$C_4$)-alkyl,
R17 is hydrogen atom or —($C_1$-$C_4$)-alkyl and
X is Cl, Br or I.

The aprotic solvent useful for step 1 in the process of the present invention must be solvent, wherein the compounds of formulae II, III and IV, palladium catalyst, base and ligand are soluble or at least partially soluble and compatible and is chemically inert under the reaction conditions and does not contain water or oxygen as impurities. Examples of said aprotic solvents are: benzene, toluene, xylene, mesitylene, acetonitrile, tetrahydrofuran, dimethylformamide, n-methylpyrrolidinone, dimethylacetamide, dimethylsulfoxide, diglyme ((2-methoxyethyl)ether) or pyridine. Preferred is benzene, mesitylene or toluene. Most preferred is toluene.

The base useful in this process of the present invention is a basic organic or inorganic compound and acts as proton acceptor without inhibiting the catalytic activity of the employed palladium species or preventing the coupled intermediate species of the compound of formula IV to undergo the reductive aminocyclization. Suitable classes of such bases are for example carbonates, phosphates, fluorides, alkoxides and hydroxides with a suitable metal as counter ion. Carbonates and phosphates are the preferred bases in the process of the present invention. Potassium carbonate or potassium phosphate and in particular cesium carbonate are the preferred bases.

The bases are generally employed in moderate excess based on the 2-halo-nitroarene of the compound of formula II. A useful range is a 1.1 to 2 fold excess based on the 2-halo-nitroarene of the compound of formula II. The base may be favorably employed in a 1.4 fold excess based on the 2-halo-nitroarene of the compound of formula I.

The palladium catalyst useful in this process can be selected from the following classes: Pd-alkanoates, Pd-alkanoate complexes, Pd-acetonates, Pd-halides, Pd-halide complexes, Pd-phosphine complexes. Representative examples include, but are not limited to: palladium (II) acetate, palladium (II) trifluoroacetate, tris(dibenzylideneacetone)dipalladium(0), tris(dibenzylideneacetone)dipalladium(0) chloroform adduct, palladium (II) chloride, 2,2'-bis(diphenylphosphino)-1,1'-binaphthylpalladium(II) chloride, acetato(2'-di-tert-butylphosphino-1,1'-biphenyl-2-yl)palladium(II), (1,2-Bis(diphenylphosphino)ethane)dichloropalladium(II), Bis[1,2-bis(diphenylphosphino)ethane]palladium (0), [(2S,3S)-Bis(diphenylphosphino)butane] [eta3-allyl]palladium(II) perchlorate, 1,3-bis(2,4,6-trimethylphenyl)imidazol-2-ylidene(1,4-naphthoqui none)palladium (0) dimer. The preferred catalysts are palladium (II) acetate, 2,2'-bis(diphenylphosphino)-1,1'-binaphthylpalladium(II) and in particular palladium (II) trifluoroacetate.

The palladium catalyst is generally employed in an amount in the range of 1 to 10 mole percent based on the 2-halo-nitroarene of the compound of formula II. A useful range is 1 to 9 mole percent of palladium catalyst based on the 2-halo-nitroarene of the compound of formula I.

The ligand useful in this process is a mono- or bidentate phosphine ligand and can be selected from the following compounds, but are not limited to: (+/−)-2,2'-bis(diphenylphosphino)-1,1'-binaphthalene, (9,9-dimethyl-9h-xanthene-4,5-diyl)bis[diphenyl phosphine], (R)-(−)-1-[(S)-2-(diphenylphosphino)ferrocenyl]ethyldicyclohexylphosphine, 1,2-Bis(diphenylphosphino)ethane, 1,3-Bis(diphenylphosphino)propane, (R)-(−)-1-[(S)-2-(Dicyclohexylphosphino)ferrocenyl]-ethyldi-tert-butylphosphine, (R)-(+)-1,1'-Bis(diphenylphosphino)-2,2'-bis(N,N-diiisopropylamido)ferrocene, (S,S)-1-[1-(Di-tert-butylphosphino)ethyl]-2-(diphenylphosphino)ferrocene, (1R,2R)-(+)-1,2-Diaminocyclohexane-N,N'-bis(2-diphenylphosphino-1-naphthoyl, (−)-1,2-Bis((2S,5S)-2,5-diisopropylphospholano)-benzene, Bis[(2-diphenylphosphino)phenyl]ether, (S)-(−)-2,2'-Bis(di-para-tolylphosphino)-1,1'-binaphyl, 4,5-Bis(bis(3,5-bis(trifluoromethyl)phenyl)phosphino)-9,9-dimethylxanthen, 2,2'-bis[(2',4',6'-triisopropyl)dicyclohexylphosphino]-biphenyl, 2,2'-bis(di-tert-butylphosphino)biphenyl, tri-tert-butylphosphine.

Most favorably (+/−)-2,2'-bis(diphenylphosphino)-1,1'-binaphthalene or (9,9-dimethyl-9h-xanthene-4,5-diyl)bis[diphenyl phosphine] are employed in particular in combination with a palladium source bearing no phosphine itself, like e.g. palladium (II) acetate, palladium (II) trifluoroacetate, tris(dibenzylideneacetone)dipalladium(0), palladium (II) chloride. The most preferred ligand is (+/−)-2,2'-bis(diphenylphosphino)-1,1'-binaphthalene.

The phosphine ligand is generally employed in an amount in the range of 1 to 10 mole percent based on the 2-halo-nitroarene of the compound of the compound of formula II. A useful range is 1 to 9 mole percent of phosphine ligand based on the 2-halo-nitroarene of the compound of formula II. Most favorably the phosphine ligand is employed in an equimolar ratio with respect to the palladium source.

The reaction step 1 is carried out in the temperature range 60° C. to 150° C. A useful temperature is about 70° C. to 90° C. Generally the reaction is carried out under the exclusion of air and moisture such as under an inert atmosphere like e.g. in an argon or nitrogen atmosphere at atmospheric pressure. The reaction time for step 1 is in the range of 3 to 48 hours (h).

It is possible to filtrate or to isolate the compound of formula IV before reacting it in the second step. It is also possible to perform reaction step 2 without any separation step in the same reaction vessel.

The solvent useful for step 2 or the second solvent in the process of the present invention is an aprotic or protic solvent, wherein the compounds of formula IV or I are soluble or at least partially soluble and compatible with the reaction conditions and involved structures and reagents. Examples of said aprotic or protic solvents are: methanol, ethanol, propanol, acetic acid, methylene chloride, dimethylformamide, tetrahydrofuran, pyridine, p-xylene, ethylacetate, benzene, toluene, xylene, mesitylene or acetonitrile. Preferred are methanol, ethanol, acetic acid, methylene chloride, dimethylformamide, pyridine, p-xylene and isopropanol. Most preferred is acetic acid. The reducing reagent useful for the reductive aminocyclization in step 2 in the process of the present invention can be selected from the following examples, but are not limited to: $H_2$/Raney-Ni, $H_2$/Pd—C, $H_2$/PtO$_2$, $H_2$/Ru, $NaBH_4$/$NiCl_2$, $NaBH_4$/$FeCl_2$, $H_3PO_2$/Pd—C, Sn/HCl, $SnCl_2$/HCl, Fe/HOAc, Fe/HCl, $FeSO_4$/HCl, Fe/$FeSO_4$, Zn/HCl, $Na_2S$, and $Na_2S_2O4$. Favorable is Fe/HOAc as a reagent for the reductive aminocyclization.

The reaction step 2 is carried out in the temperature range 80° C. to 140° C. A useful temperature is about 110° C. to 120° C. The reaction time for step 2 is in the range of 15 min to 120 min.

The progress of each reaction step may be monitored by methods known to those skilled in the art, like for example thin layer silica gel chromatography, gas chromatography, nuclear magnetic resonance, infrared spectroscopy, and high pressure liquid chromatography combined with ultraviolet detection or mass spectroscopy. Preferably thin layer silica gel chromatography and high pressure liquid chromatography (HPLC) combined with mass spectroscopy are used.

The isolation and purification procedures useful for the compounds obtained by the process of the present invention are well-known to those skilled in the art, like for example filtration through a Celite containing cartridge, aqueous work-up, extraction with organic solvents, distillation, crystallization, chromatography on silica, and high pressure liquid chromatography on normal phase or reversed phase. Preferred methods include, but are not limited to those exemplified.

The term alkyl as used herein expressly includes saturated groups as well as unsaturated groups which latter groups contain one or more, for example one, two or three, double bonds and/or triple bonds. All these statements also apply if an alkyl group occurs as a substituent on another residue, for example in an alkyloxy residue, an alkyloxycarbonyl residue or an arylalkyl residue. Examples of "—$(C_1-C_8)$-alkyl" or "—$(C_1-C_8)$-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl or tert-pentyl. Unsaturated alkyl residues are e.g. alkenyl residues such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl, or alkynyl residues such as ethynyl, 1-propynyl, 2-propynyl (=propargyl) or 2-butynyl. Alkyl residues can also be unsaturated when they are substituted.

The term "—$(C_3-C_8)$-cycloalkyl" is understood as cyclic alkyl residues are cycloalkyl residues containing 3, 4, 5, 6, 7 or 8 ring carbon atoms like cyclopropyl, cyclobutyl, cyclopentyl, cyclohexyl, cycloheptyl or cyclooctyl, which can also be substituted and/or unsaturated. Unsaturated cyclic alkyl groups and unsaturated cycloalkyl groups like, for example, cyclopentenyl or cyclohexenyl can be bonded via any carbon atom. The term "A1, A2, A3, A4 are independently from each other selected from carbon or nitrogen atoms to form together with the two carbon atoms in formula I a stable aromatic or heteroaromatic ring" refers to a residue which can be derived from compounds such as benzene, pyrazine, pyridazine, pyridine, pyrimidine, triazine or tetrazine.

The term "—$(C_6-C_{14})$-aryl" is understood as meaning aromatic hydrocarbon radicals containing from 6 to 14 carbon atoms in the ring. Examples of —$(C_6-C_{14})$-aryl radicals are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals.

The term "—$(C_4-C_{14})$-heteroaryl" refers to mono-, di- or tri-ring systems, wherein one or more of the 4 to 14 ring carbon atoms are replaced by heteroatoms such as nitrogen, oxygen or sulfur. Examples are acridinyl, azaindole (1H-pyrrolopyridinyl), azabenzimidazolyl, azaspirodecanyl, azepinyl, azetidinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl. The term "a 3- to 7-membered cyclic residue, containing 1, 2, 3 or 4 heteroatoms" refer to structures of heterocycles, which can be derived from compounds such as azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The 3- to 7-membered monocyclic group may be bonded via any ring carbon atom, and in the case of nitrogen heterocycles via any suitable ring nitrogen atom. Thus, for example, a pyrrolyl residue can be 1-pyrrolyl, 2-pyrrolyl or 3-pyrrolyl, a pyrrolidinyl residue can be pyrrolidin-1-yl (=pyrrolidino), pyrrolidin-2-yl or pyrrolidin-3-yl, a pyridinyl residue can be pyridin-2-yl, pyridin-3-yl or pyridin-4-yl, a piperidinyl residue can be piperidin-1-yl (=piperidino), piperidin-2-yl, piperidin-3-yl or piperidin-4-yl. Furyl can be 2-furyl or 3-furyl, thienyl can be 2-thienyl or 3-thienyl, imidazolyl can be imidazol-1-yl, imidazol-2-yl, imidazol-4-yl or imidazol-5-yl, 1,3-oxazolyl can be 1,3-oxazol-2-yl, 1,3-oxazol-4-yl or 1,3-oxazol-5-yl, 1,3-thiazolyl can be 1,3-thiazol-2-yl, 1,3-thiazol-4-yl or 1,3-thiazol-5-yl, pyrimidinyl can be pyrimidin-2-yl, pyrimidin-4-yl (=6-pyrimidinyl) or 5-pyrimidinyl, piperazinyl can be piperazin-1-yl (=piperazin-4-yl=piperazino) or piperazin-2-yl.

The term "R1 and R2, R2 and R3 or R3 and R4 form together with the atoms which they are attached to a 5- or 8-membered ring, containing 0, 1, 2, 3 or 4 heteroatoms chosen from nitrogen, sulfur or oxygen" refers to residues which can be derived from compounds such as azepine, azirine, azocane, azocane-2-one, cycloheptyl, cyclohexyl, cyclooctane, cyclooctene, 1,4-diazepane, 1,2-diazepine, 1,3-diazepine, 1,4-diazepine, [1,2]diazocan-3-one, [1,3]diazocan-2-one, [1,4]diazocane, dioxazine, dioxazole, [1,4]dioxocane, 1,3-dioxolane, dioxole, 1,3-dioxolene, furan, imidazole, imidazolidine, imidazoline, isothiazole, isothiazolidine, isothiazoline, isothiazole, isoxazole, isoxazolidine, isoxazoline, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxaziridine, [1,4]oxazocane, [1,3]oxazocan-2-one, oxocane, oxocan-2-one, oxazole, piperidine, piperazine, phenyl, pyridazine, pyridine, pyrimidine, pyran, pyrazine, pyrazole, pyrazolepyrrole, pyrazolidine, pyrazoline, pyridazine, pyridine, pyrimidine, pyrrole, pyrrolidine, pyrrolidinone, pyrroline, 5,6,7,8-tetrahydro-1H-azocin-2-one, tetrahydrofuran, tetrahydropyran, tetrahydropyridine, tetrazine, tetrazole, thiadiazine, thiadiazole, 1,2-thiazine, 1,3-thiazine, 1,4-thiazine, thiazole, 1,3-thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The fact that many of the before-listed names of heterocycles are the chemical names of unsaturated or aromatic ring systems does not imply that the, 4- to 14-membered mono- or polycyclic group could only be derived from the respective unsaturated ring system. The names here only serve to describe the ring system with respect to ring size and the number of the heteroatoms and their relative positions. As explained above, the 4- to 14-membered mono- or polycyclic group can be saturated or partially unsaturated or aromatic, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles from which this group may be derived the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), perhydro-1,4-thiazine (=thiomorpholine), perhydroazepine, indoline, isoindoline, 1,2,3,4-tetrahydroquinoline or 1,2,3,4-tetrahydroisoquinoline.

The term "—$(C_1$-$C_3)$-fluoroalkyl" is a partial or totally fluorinated alkyl-residue, which can be derived from residues such as —$CF_3$, —$CHF_2$, —$CH_2F$, —$CHF$—$CF_3$, —$CHF$—$CHF_2$, —$CHF$—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—$CHF$—$CF_3$, —$CH_2$—$CHF$—$CHF_2$, —$CH_2$—$CHF$—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —$CHF$—$CHF$—$CF_3$, —$CHF$—$CHF$—$CHF_2$, —$CHF$—$CHF$—$CH_2F$, —$CHF$—$CH_2$—$CF_3$, —$CHF$—$CH_2$—$CHF_2$, —$CHF$—$CH_2$—$CH_2F$, —$CHF$—$CF_2$—$CF_3$, —$CHF$—$CF_2$—$CHF_2$, —$CHF$—$CF_2$—$CH_2F$, —$CF_2$—$CHF$—$CF_3$, —$CF_2$—$CHF$—$CHF_2$, —$CF_2$—$CHF$—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

Halogen is fluorine, chlorine, bromine or iodine, preferably fluorine, chlorine or bromine, particularly preferably chlorine or bromine.

The term "triflate" refers to trifluoro-methanesulfonic acid ester or trifluoromethanesulfonate.

The term "nonaflate" refers to 1,1,2,2,3,3,4,4,4-nonafluoro-1-butanesulfonic acid ester or 1,1,2,2,3,3,4,4,4-nonafluoro-1-butanesulfonate.

The term "at least one of R1, R2, R3 or R4 are absent in case one or more of A1, A2, A3 or A4 are nitrogen atom," refers to a residue wherein the nitrogen atom is not substituted by any residue, e.g. in case A1 is nitrogen atom and A2, A3 and A4 are each a carbon atom and R4 is absent and R1, R2 and R3 are each a hydrogen atom the residue pyridine is formed. If R1, R2 and R3 are not each a hydrogen atom but one of the residues specified under b) to x) then a substituted pyridine residue is formed. In case A1 and A2 are each a nitrogen atom and A3 and A4 are each a carbon atom and R4 and R3 are absent and R1 and R2 are each a hydrogen atom the residue pyridazine is formed. If R1 and R2 are not each a hydrogen atom but one of the residues specified under b) to x) then a substituted pyridazine residue is formed.

Optically active carbon atoms present in the compounds of the formula (I) can independently of each other have R configuration or S configuration. The compounds of the formula (I) can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula (I), and it comprises all ratios of the stereoisomers in the mixtures. In case the compounds of the formula (I) can be present as E isomers or Z isomers (or cis isomers or trans isomers) the invention relates both to pure E isomers and pure Z isomers and to E/Z mixtures in all ratios. The invention also comprises all tautomeric forms of the compounds of the formula (I).

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula (I) can also be obtained by employing stereochemically uniform starting materials or by using stereoselective reactions.

Especially preferred compounds of the formula (I) are those wherein two or more residues are defined as indicated before for preferred compounds of the formula (I), or residues can have one or some of the specific denotations of the residues given in their general definitions or in the definitions of preferred compounds before. All possible combinations of definitions given for preferred definitions and of specific denotations of residues explicitly are a subject of the present invention.

The starting materials or building blocks for use in the general synthetic procedures that can be applied in the preparation of the compounds of formula (I) are readily available to one of ordinary skill in the art. In many cases they are commercially available or have been described in the literature. Otherwise they can be prepared from readily available precursor compounds analogously to procedures described in the literature, or by procedures or analogously to procedures described in this application.

Further, in order to obtain the desired substituents in the benzene nucleus and in the heterocyclic nucleus of the benzimidazole or azabenzimidazole ring system in the formula (I), the functional groups introduced into the ring system during the benzimidazole or azabenzimidazole synthesis can be chemically modified. For example, benzimidazoles carrying a hydrogen atom in the 2-position can also be obtained by oxidation of 2-methyl benzimidazole to the benzimidazole-2-carboxylic acid and subsequent decarboxylation or from benzimidazoles carrying an ester group in the respective position. Carboxylic acid groups and acetic acid groups in the 2-position can be converted into their homologues by usual reactions for chain elongation of carboxylic acids.

Especially the groups present in the benzimidazole or azabenzimidazole ring system can be modified by a variety of reactions and thus the desired residues R0, R1, R2, R3, R4 and R5 be obtained. For example, nitro groups can be reduced to amino group with under the described reaction conditions or by various reducing agents, such as sulfides, dithionites, complex hydrides or by catalytic hydrogenation. A reduction of a nitro group may also be carried out at a later stage of the synthesis of a compound of the formula (I), and a reduction of a nitro group to an amino group may also occur simultaneously with the reaction performed on another functional group, for example when reacting a group like a cyano group with hydrogen sulfide or when hydrogenating a group. Ester groups present in the benzene nucleus can be hydrolyzed to the corresponding carboxylic acids, which after activation can then be reacted with amines or alcohols under standard conditions. Ether groups present at the benzene nucleus, for example benzyloxy groups or other easily cleavable ether groups, can be cleaved to give hydroxyl groups which then can be reacted with a variety of agents, for example etherification agents or activating agents allowing replacement of the hydroxyl group by other groups. Sulfur-containing groups can be reacted analogously.

Due to the fact that in the present case the functional groups are attached to an benzimidazole or azabenzimidazole ring it may in certain cases become necessary to specifically adapt reaction conditions or to choose specific reagents from a variety of reagents that can in principle be employed into a conversion reaction, or otherwise to take specific measures for achieving a desired conversion, for example to use protection group techniques. However, finding out suitable reaction variants and reaction conditions in such cases does not cause any problems for one skilled in the art.

In the course of the preparation of the compounds of the formula I it can generally be advantageous or necessary to introduce functional groups which reduce or prevent undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991, or P. Kocienski, Protecting Groups, Thieme 1994). As example of a precursor group cyano groups may be mentioned which can in a later step be transformed into carboxylic acid derivatives or by reduction into aminomethyl groups? Protective groups can also have the meaning of a solid phase, and cleavage from the solid phase stands for the removal of the protective group. The use of such techniques is known to those skilled in the art (Burgess K (Ed.) Solid Phase Organic Synthesis, New York: Wiley, 2000). For example, a phenolic hydroxy group can be attached to a trityl-polystyrene resin, which serves as a protecting group, and the molecule is cleaved from this resin by treatment with TFA at a later stage of the synthesis.

In the course of the synthesis the employment of microwave assistance for speeding-up, facilitating or enabling reactions may be beneficial or even required in many cases. Some reactions are for example described by J. L. Krstenansky, I. Cotteril, Curr. Opin. Drug. Disc. & Development., 4(2000), 454; P. Lidstrom, J. Tierney, B. Wathey, J. Westman, Tetrahedron, 57 (2001), 9225; M. Larhed, A. Hallberg, Drug Discovery Today, 8 (2001) 406; S. Caddick, Tetrahedron, 51 (1995) 10403.

Physiologically tolerable salts of the compounds of formula I are nontoxic salts that are physiologically acceptable, in particular, pharmaceutically utilizable salts. Such salts of compounds of formula I containing acidic groups, for example, a carboxyl group (COOH), include, for example, alkali metal salts or alkaline earth metal salts, such as sodium salts, potassium salts, magnesium salts and calcium salts, as well as salts with physiologically tolerable quaternary ammonium ions, such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of formula I, for example, amino groups or guanidino groups, form acid addition salts, for example, with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I which simultaneously contain a basic group and an acidic group, for example, a guanidino group and a carboxyl group, can also be present as zwitterions (betaines) which are likewise included in the scope of the present invention.

Salts of compounds of formula I can be obtained by customary methods known to those skilled in the art, for example, by combining a compound of the formula I with an inorganic or organic acid or base in a solvent or dispersant, or from other salts by cation exchange or anion exchange. The present invention also includes all salts of the compounds of formula I which, because of low physiologically tolerability, are not directly suitable for use in pharmaceuticals but are suitable, for example, as intermediates for carrying out further chemical modifications of the compounds of formula I or as starting materials for the preparation of physiologically tolerable salts.

A further aspect of the invention is the use of a compound of the formula I as prepared by the process according to the invention for the production of pharmaceuticals, diagnostic agents, liquid crystals, polymers, herbicides, fungicidals, nematicidals, parasiticides, insecticides, acaricides and arthropodicides.

Preferred methods include, but are not limited to those described in the examples. Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequences for preparing the compounds useful in the present invention are outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

EXAMPLES

When in the final step of the synthesis of a compound an acid such as trifluoroacetic acid or acetic acid was used, for example when trifluoroacetic acid was employed to remove a tBu group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt or hydrochloric acid salt.

Abbreviations Used:

tert-Butyl tBu 2,2'-bis(diphenylphosphino)-1,1'-binaphthalene BINAP

Calculated cal dibenzylidenacetone dba

Dimethylsulfoxide DMSO 1,1'-Bis(diphenylphosphino)ferrocene DPPF

Fast atom bombardment FAB

High pressure liquid chromatography HPLC

Liquid chromatography with mass spectrometry LC-MS

Melting point mp

Acetic acid HOAc

Trifluoroacetic acid TFA 4,5-Bis(diphenylphosphino)-9,9-dimethylxanthene Xantphos Example 1

5-Chloro-2-methyl-1-phenyl-1H-benzimidazole

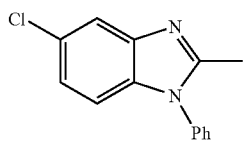

Method A: The 2,5-dichloronitrobenzene (96 mg, 0.5 mmol), N-phenyl-acetamide (81 mg, 0.6 mmol), palladium trifluoroacetate (13 mg, 0.04 mmol), BINAP (24 mg, 0.08 mmol) and cesium carbonate (212 mg, 0.7 mmol) were placed in a reaction tube, which was then purged with dry argon. Dry toluene (3 mL) was added, and the mixture was heated at 80° C. for 18 hours (h). The reaction was hydrolyzed with 3 mL of water and filtered through a Varian cartridge Chem Elut 12198007, rinsing with ethyl acetate. The crude was dissolved in 10 mL of glacial acetic acid and refluxed for 30 min in the presence of iron powder (279 mg, 5 mmol). The acid was removed under reduced pressure and the residue was suspended in saturated sodium bicarbonate solution and extracted with ethyl acetate. The obtained crude was purified by preparative HPLC, affording the title compound as a yellow solid (114 mg, 94% yield). mp 109-111° C. $^1$H NMR (DMSO) δ 2.52 (s, 3H), 7.22 (d, J=8.6Hz, 1H), 7.34 (d, J=8.6Hz, 1H), 7.48-7.59 (m, 5H), 7.86 (s, 1H); $^{13}$C NMR δ 13.5, 112.2, 116.4, 123.9, 126.9, 127.9, 129.7, 130.1, 133.9, 138.5, 154.0, 157.0. HRMS (FAB): cal. for $C_{14}H_{12}N_2Cl$ [M+H$^+$]: 243.0689; found: 243.0684.

Method B (One-Pot Procedure): The first reaction step is performed as described in method A. After heating at 80° C. for 18 h, the iron powder and glacial acetic acid are directly added. Then the reaction mixture is heated at reflux for 30 min. Work-up and product purification is conducted in analogy to method A, obtaining 93 mg of the title compound (77% yield).

Method C: the title compound was also obtained using a smaller amount of a different catalyst, and also smaller amount of ligand, as method A was followed with 2,5-dichloronitrobenzene (96 mg, 0.5 mmol), N-phenyl-acetamide (81 mg, 0.6 mmol), palladium acetate (2.2 mg, 0.01 mmol), BINAP (6 mg, 0.02 mmol) and cesium carbonate (212 mg, 0.7 mmol), obtaining 80 mg of the title compound (66% yield).

Example 2

2-Methyl-1-phenyl-1H-benzimidazole

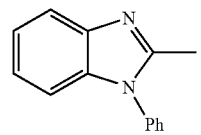

Method A afforded the title compound from 2-chloronitrobenzene (79 mg, 0.5 mmol) and N-phenyl-acetamide (81 mg, 0.6 mmol) as a yellow solid (82 mg, 78% yield). mp 46-48° C. $^1$H NMR δ 2.63 (m, 3H), 7.32 (d, J=Hz, 1H), 7.47 (t, J=Hz, 1H), 7.53 (t, J=Hz, 1H), 7.66-7.72 (m, 5H), 7.88 (d, J=7.2Hz, 2H); $^{13}$C NMR δ 12.6, 111.8, 115.1, 125.3, 127.1, 130.2, 130.3, 132.9, 133.8, 152.2, 158.3. HRMS (FAB): cal. for $C_{14}H_{13}N_2$ [M+H$^+$]: 209.1079; found: 209.1072. The same product was obtained from 2-bromonitrobenzene (101 mg, 0.5 mmol) in 80% yield (83 mg), and from 2-iodonitrobenzene (125 mg, 0.5 mmol) in 81% yield (84 mg).

Method C afforded 83 mg the title compound (80% yield).

Example 3

7-Chloro-2-methyl-1-phenyl-1H-benzimidazole

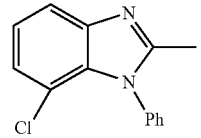

Method A applied to 2,3-dichloronitrobenzene (96 mg, 0.5 mmol) and N-phenylacetamide (81 mg, 0.6 mmol) yielded the title compound as a brown solid (81 mg, 67%). mp 103-105° C. $^1$H NMR (DMSO) δ 2.38 (s, 3H), 7.30-7.33 (m, 2H), 7.56-7.62 (m, 5H), 7.70 (dd, J=5.4, 3.7Hz, 1H); $^{13}$C NMR δ 13.2, 115.9, 116.0, 124.5, 125.0, 128.7, 129.3, 130.2, 134.6, 138.9, 153.7, 158.5. HRMS (FAB): cal. for $C_{14}H_{12}N_2Cl$ [M+H$^+$]: 243.0689; found: 243.0683.

Example 4

2,7-Dimethyl-1-phenyl-1H-benzimidazole

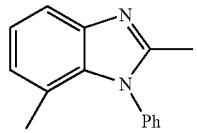

Method A applied to 2-chloro-3-nitrotoluene (68 mg, 0.5 mmol) and N-phenylacetamide (81 mg, 0.6 mmol) yielded the title compound as a pale yellow solid. mp 107-109° C. $^1$H NMR (DMSO) δ 1.83 (s, 3H), 2.34 (s, 3H), 7.02 (d, J=7.8Hz, 1H), 7.22 (t, J=7.8 Hz, 1H), 7.53 (d, J=7.8Hz, 1H), 7.55-7.63 (m, 5H); $^{13}$C NMR δ 13.3, 17.1, 114.8, 121.7, 123.0, 125.5, 128.6, 129.4, 129.9, 136.0, 144.5, 151.2, 157.2. HRMS (FAB): cal. for $C_{15}H_{15}N_2$ [M+H$^+$]: 223.1235; found: 223.1231.

Method C afforded 85 mg of the title compound (77% yield).

Example 5

5-Methoxy-2-methyl-1-phenyl-1H-benzimidazole

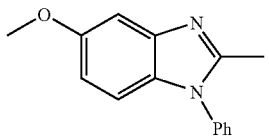

Method A applied to 4-chloro-3-nitroanisol (84 mg, 0.5 mmol) and N-phenylacetamide (81 mg, 0.6 mmol) yielded the title compound as a pale yellow solid. mp 88-90° C. $^1$H NMR (DMSO) δ 2.61 (s, 3H), 3.88 (s, 3H), 7.07 (d, J=8.9Hz, 1H), 7.25 (d, J=8.9 Hz, 1H), 7.38 (br s, 1H), 7.65-7.73 (m, 5H); $^{13}$C NMR δ 12.5, 55.9, 97.7, 112.6, 114.7, 126.9, 127.8, 130.2, 130.3, 132.8, 133.1, 151.2, 157.6, 157.8. HRMS (FAB): cal. for $C_{15}H_{15}N_2O$ [M+H$^+$]: 239.1184; found: 239.1180.

Example 6

2-Methyl-1-phenyl-1H-benzimidazole-5-carboxylic Acid Methyl Ester

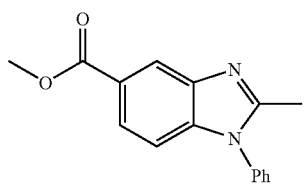

The title compound was prepared following Method A at larger scale, from 4-chloro-3-nitrobenzoic acid methyl ester (5.39 g, 25 mmol), N-phenylacetamide (3.38 g, 25 mmol), palladium trifluoroacetate (416 mg, 1.25 mmol), BINAP (778 mg, 1.25 mmol) and Cs$_2$CO$_3$ 11.4 g, 35 mmol) and refluxing just for 5 hours, giving rise to the title compound as colorless crystals (5.19 g, 78%). mp 108° C. to 110° C. $^1$H NMR (DMSO) δ 2.55 (s, 3H), 3.78 (s, 3H), 7.30 (d, J=8.2Hz, 1H), 7.52-7.71 (m, 5H), 7.92 (d, J=8.2Hz, 1H), 8.30 (br s, 1H); $^{13}$C NMR δ 13.6, 52.1, 110.8, 118.5, 124.7, 124.8, 127.0, 129.7, 130.1, 134.0, 137.9, 153.7, 157.8, 166.2. HRMS (FAB): cal. for $C_{16}H_{15}N_2O_2$ [M+H$^+$]: 267.1134; found: 267.1128.

Example 7

2-Methyl-1-phenyl-1H-benzimidazole-5-carbaldehyde

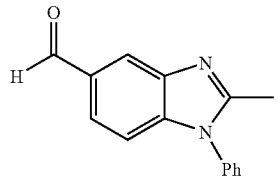

Method A applied to 4-dimethoxymethyl-1-iodo-2-nitrobenzene (155 mg, 0.5 mmol) and N-phenylacetamide (81 mg, 0.6 mmol) yielded the title compound as pale yellow oil (79 mg, 67% yield). $^1$H NMR (DMSO) δ 2.50 (s, 3H), 7.31 (d, J=8.3Hz, 1H), 7.61-7.68 (m, 5H), 7.82 (d, J=8.3Hz, 1H), 8.25 (s, 1H), 10.10 (s, 1H); $^{13}$C NMR δ 13.6, 111.4, 120.1, 124.2, 127.0, 129.8, 130.2, 132.3, 139.1, 154.7, 158.3, 192.4. HRMS (FAB): cal. for $C_{15}H_{13}N_2O$ [M+H$^+$]: 237.1028; found: 237.1024.

Example 8

1,2-Diphenyl-1H-benzimidazole

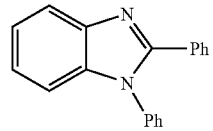

Method A applied to 1-iodo-2-nitrobenzene (125 mg, 0.5 mmol) and benzanilide (118 mg, 0.6 mmol) yielded the title compound as pale yellow solid (112 mg, 83%). mp 105-107° C. $^1$H NMR (DMSO) δ 7.24 (d, J=7.9Hz, 1H), 7.35-7.62 (m, 12H), 7.84 (d, J=7.6Hz, 1H); $^{13}$C NMR δ 111.0, 118.1, 123.7, 124.1, 127.5, 127.9, 128.4, 129.2, 129.3, 130.0, 130.2, 135.5, 136.2, 139.3, 151.3. HRMS (FAB): cal. for $C_{19}H_{15}N_2$ [M+H$^+$]: 271.1235; found: 271.1230.

Example 9

1-Phenyl-2-pyridin-3-yl-1H-benzimidazole

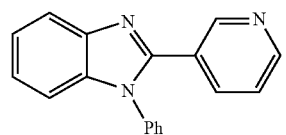

Method A applied to 1-iodo-2-nitrobenzene (125 mg, 0.5 mmol) and nicotinanilide (119 mg, 0.6 mmol) yielded the title compound as brown solid (68 mg, 50%). mp 110-112° C. $^1$H NMR (DMSO) δ 7.26 (d, J=7.3Hz, 1H), 7.32-7.63 (m, 8H), 7.86 (d, J=7.6 Hz, 1H), 7.89 (d, J=7.8Hz, 1H), 8.62 (d, J=3.0Hz, 1H), 8.72 (br s, 1H); $^{13}$C NMR δ 111.0, 118.7, 123.8, 124.0, 124.4, 125.4, 127.6, 129.5, 130.2, 135.2, 136.4, 137.7, 140.3, 148.6, 149.6, 158.3. HRMS (FAB): cal. for $C_{18}H_{14}N_3$ [M+H$^+$]: 272.1188; found: 272.1180.

Example 10

1-Phenyl-2-tridecyl-1H-benzimidazole

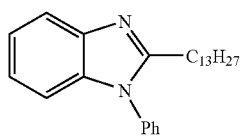

Method A applied to 1-iodo-2-nitrobenzene (125 mg, 0.5 mmol) and myristanilide (182 mg, 0.6 mmol) yielded the title compound as colorless oil (130 mg, 69%). $^1$H NMR (DMSO) δ 0.74 (t, J=6.9Hz, 3H), 1.14-1.28 (m, 20H), 1.68 (p, J=7.6Hz, 2H), 2.83 (t, J=7.6Hz, 2H), 7.14 (d, J=8.1Hz, 1H), 7.29 (dd, J=8.1, 7.7Hz, 1H), 7.47 (dd, J=8.1, 7.7Hz, 1H), 7.56-7.68 (m, 5H), 7.74 (d, J=7.7Hz, 1H); $^{13}$C NMR δ 13.9, 22.0, 26.3, 26.4, 28.3, 28.4, 28.7, 28.8, 28.9, 29.9, 31.2, 110.7, 116.9, 123.5, 123.7, 127.2, 129.6, 130.1, 134.2, 135.0, 137.6, 154.7. HRMS (FAB): cal. for $C_{26}H_{36}N_2$ [M+H$^+$]: 377.2957; found: 377.2953. Method C afforded 149 mg of the title compound (79% yield).

Example 11

1,2-dimethyl-1H-benzimidazole

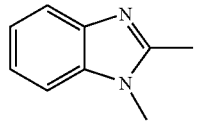

Method A applied to 1-iodo-2-nitrobenzene (125 mg, 0.5 mmol) and N-methylacetamide (44 mg, 0.6 mmol) yielded the title compound as pale yellow solid (62 mg, 85%). mp 101° C. to 103° C. $^1$H NMR (DMSO) δ 2.79 (s, 3H), 3.92 (s, 3H), 7.46-7.55 (m, 2H), 7.78 (d, J=7.4Hz, 1H), 7.89 (d, J=7.1Hz, 1H); $^{13}$C NMR δ 11.6, 30.8, 112.3, 114.1, 124.9, 125.3, 132.6, 151.9, 158.3. HRMS (FAB): cal. for $C_9H_{11}N_2$ [M+H$^+$]: 147.0922; found: 147.0917. Method C afforded 38 mg of the title compound (52% yield).

Example 12

2-Methyl-1-phenethyl-1H-benzimidazole

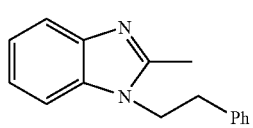

Method A applied to 1-iodo-2-nitrobenzene (125 mg, 0.5 mmol) and N-phenylethylacetamide (98 mg, 0.6 mmol) yielded the title compound as pale yellow solid (54 mg, 46%). mp 104° C. to 106° C. $^1$H NMR (DMSO) δ 2.51 (s, 3H), 3.10 (d, J=7.0Hz, 2H), 4.63 (d, J=7.0Hz, 2H), 7.09-7.52 (m, 7H), 7.72 (d, J=4.6Hz, 1H), 7.84 (d, J=4.6Hz, 1H); $^{13}$C NMR δ 11.1, 34.1, 45.8, 112.5, 114.2, 125.1, 125.5, 126.9, 128.5, 128.9, 131.6, 137.2, 151.2, 158.0. HRMS (FAB): cal. for $C_{16}H_{17}N_2$ [M+H$^+$]: 237.1392; found: 237.1383.

Example 13

2-Methyl-1-pyridin-2-yl-1H-benzimidazole

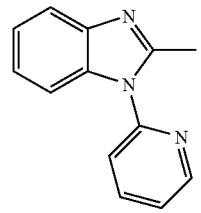

Method A applied to 1-iodo-2-nitrobenzene (125 mg, 0.5 mmol) and 2-acetamido-pyridine (82 mg, 0.6 mmol) yielded the title compound as brown solid (40 mg, 38%). mp 121-123° C. $^1$H NMR (DMSO) δ 2.69 (s, 3H), 7.36-7.46 (m, 2H), 7.53 (d, J=7.4 Hz, 1H), 7.68 (dd, J=7.6, 4.7Hz, 1H), 7.77 (d, J=7.6Hz, 1H), 7.81 (d, J=7.9Hz, 1H), 8.21 (dd, J=7.9, 7.6Hz, 1H), 8.75 (d, J=4.7Hz); $^{13}$C NMR δ 13.6, 112.0, 116.1, 121.0, 124.7, 124.9, 133.0, 135.2, 140.1, 147.2, 150.0, 151.7, 157.9. HRMS (FAB): cal. for $C_{13}H_{12}N_3$ [M+H$^+$]: 210.1031; found: 210.1025.

Example 14

5-(1-Phenyl-1H-benzoimidazol-2-yl)-pentanoic Acid Methyl Ester

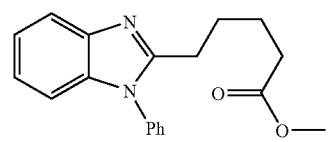

Method A applied to 1-iodo-2-nitrobenzene (125 mg, 0.5 mmol) and 5-phenylcarbamoyl-pentanoic acid methyl ester (141 mg, 0.6 mmol) yielded the title compound as brown oil (136 mg, 88%). $^1$H NMR (DMSO) δ 1.50-1.74 (m, 4H), 2.27 (d, J=7.2Hz, 2H), 2.89 (d, J=7.5Hz, 2H), 3.52 (s, 3H), 7.22 (d, J=8.1Hz, 1H), 7.38 (apparent t, J=7.6Hz, 1H), 7.46 (apparent t, J=7.6Hz, 1H), 7.52-7.72 (m, 5H), 7.79 (d, J=7.8 Hz, 1H); $^{13}$C NMR δ 23.3, 25.3, 25.4, 32.2, 50.9, 111.3, 115.6, 124.3, 124.4, 126.8, 130.0, 132.4, 133.2, 133.4, 153.9, 172.3. HRMS (FAB): cal. for $C_{19}H_{21}N_2O_2$ [M+H$^+$]: 309.1603; found: 309.1595.

Example 15

2-(5-Chloro-pentyl)-1-phenyl-1H-benzimidazole

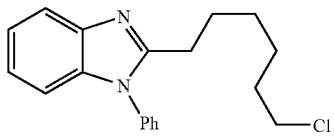

Method A applied to 1-iodo-2-nitrobenzene (125 mg, 0.5 mmol) and 7-chloro-heptanoic acid phenylamide (144 mg, 0.6 mmol) yielded the title compound as pale yellow oil (95 mg, 64%). $^1$H NMR (DMSO) δ 1.34-1.77 (m, 6H), 2.92 (t, J=7.6Hz, 2H), 3.53 (t, J=6.7Hz, 2H), 7.26 (d, J=7.8Hz, 1H), 7.43 (t, J=7.8Hz, 1H), 7.52 (d, J=8.9Hz, 1H), 7.64-7.72 (m, 5H), 7.85 (d, J=7.8Hz, 1H); $^{13}$C NMR δ 25.3, 25.5, 25.7, 31.3, 44.9, 111.5, 115.7, 124.8, 124.9, 127.2, 130.2, 130.3, 133.2, 134.1, 154.5. HRMS (FAB): cal. for $C_{18}H_{20}N_2Cl$ [M+H$^+$]: 299.1315; found: 299.1306.

Example 16

1-(4-Methoxy-phenyl)-2-methyl-1H-benzimidazole

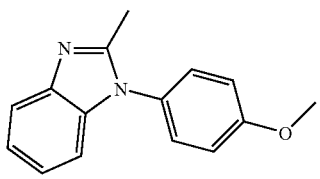

Method A applied to 1-iodo-2-nitrobenzene (125 mg, 0.5 mmol) and p-acetanisidide (99 mg, 0.6 mmol) yielded the title compound as colorless solid (107 mg, 90%). mp 121° C. to 123° C. $^1$H NMR (DMSO) δ 2.61 (s, 3H), 3.87 (s, 3H), 7.23 (d, J=9.1Hz, 2H), 7.28 (d, J=8.7Hz, 1H), 7.52 (dd, J=8.1, 7.4Hz, 1H), 7.48 (dd, J=7.8, 7.4Hz, 1H), 7.59 (d, J=9.1Hz, 2H), 7.83 (d, J=7.8Hz, 1H); $^{13}$C NMR δ 12.6, 55.6, 111.7, 115.1, 115.3, 125.1, 125.3, 128.4, 132.5, 134.1, 152.3, 158.2, 160.2. HRMS (FAB): cal. for $C_{15}H_{15}N_2O$ [M+H$^+$]: 239.1184; found: 239.1179.

Example 17

4-(2-Methyl-benzoimidazol-1-yl)-benzonitrile

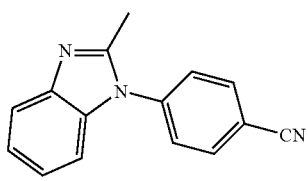

Method A applied to 1-iodo-2-nitrobenzene (125 mg, 0.5 mmol) and p-acetamidobenzo-nitrilo (96 mg, 0.6 mmol) yielded the title compound as brown solid (96 mg, 82%). mp 166° C. to 168° C. $^1$H NMR (DMSO) δ 2.62 (s, 3H), 7.33 (d, J=7.8 Hz, 1H), 7.42 (t, J=7.8Hz, 1H), 7.47 (t, J=7.8Hz, 1H), 7.89 (d, J=8.9Hz, 2H), 8.20 (d, J=8.9Hz, 2H); $^{13}$C NMR δ 13.0, 111.2, 112.6, 116.0, 117.9, 124.7, 124.8, 128.2, 133.7, 134.4, 135.0, 137.5, 151.8. HRMS (FAB): cal. for $C_{15}H_{12}N_3$ [M+H$^+$]: 234.1031; found: 234.1025.

Example 18

2-Ethoxy-4-(2-methyl-benzoimidazol-1-yl)-benzoic Acid Methyl Ester

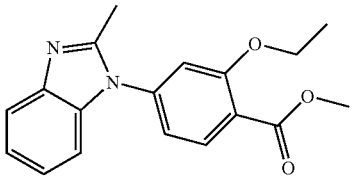

Method A applied to 1-iodo-2-nitrobenzene (125 mg, 0.5 mmol) and methyl 4-acetamido-2-ethoxybenzoate (142 mg, 0.6 mmol) yielded the title compound as pale brown oil (118 mg, 76%). $^1$H NMR (DMSO) δ1.34 (d, J=6.9Hz, 3H), 2.69 (s, 3H), 3.87 (s, 3H), 4.13 (q, J=6.9Hz, 2H), 7.32 (dd, J=8.1, 2.0Hz, 1H), 7.43-7.57 (m, 4H), 7.86 (d, J=7.8Hz, 1H), 7.92 (d, J=8.1Hz, 1H); $^{13}$C NMR δ 12.7, 14.3, 52.2, 64.7, 112.0, 112.6, 115.1, 118.5, 122.1, 125.4, 132.0, 132.5, 133.4, 136.7, 152.1, 158.3, 165.5. HRMS (FAB): cal. for $C_{18}H_{19}N_2O_3$ [M+H$^+$]: 311.1396; found: 311.1387.

Example 19

2,4-Dimethyl-1-phenyl-1H-benzimidazole

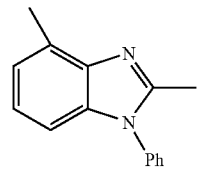

Method A applied to 3-chloro-2-nitrotoluene (86 mg, 0.5 mmol) and N-phenylacetamide (81 mg, 0.6 mmol) yielded the title compound as brown solid (37 mg, 33%). $^1$H NMR (DMSO) δ 2.46 (s, 3H), 2.55 (s, 3H), 6.88 (d, J=7.3Hz, 1H), 7.04-7.11 (m, 2H), 7.50-7.64 (m, 5H); $^{13}$C NMR δ 13.8, 16.3, 107.5, 122.5, 122.6, 126.8, 129.9, 135.1, 135.3, 150.3, 158.3.

Example 20

5-cyano-2-methyl-1-phenyl-1H-benzimidazole

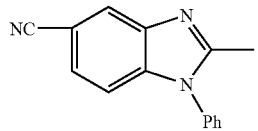

Method A applied to 4-chloro-3-nitrobenzonitrile (91 mg, 0.5 mmol) and N-phenylacetamide (81 mg, 0.6 mmol) yielded the title compound as brown solid (40 mg, 34%). $^1$H NMR (DMSO) δ 2.54 (s, 3H), 7.28 (d, J=8.3Hz, 1H), 7.52-7.59 (m, 6H), 8.12 (s, 1H); $^{13}$C NMR δ 13.8, 104.6, 111.4, 119.3, 122.7, 126.2, 127.0, 129.6, 130.1, 134.2, 138.5, 140.4, 154.6.

Example 21

2-Methyl-1-pyridin-2-yl-1H-benzimidazole

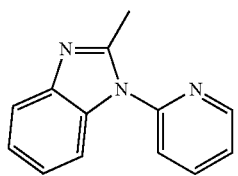

Method A applied to 1-iodo-2-nitrobenzene (125 mg, 0.5 mmol) and 2-acetamido-pyridine (82 mg, 0.6 mmol) yielded the title compound as yellowy oil (40 mg, 38%). $^1$H NMR (DMSO) δ 2.74 (s, 3H), 7.42-7.49 (m, 2H), 7.56 (d, 1H), 7.70 (dd, 1H), 7.78-7.88 (m, 2H), 8.22 (dd, 1H), 8.77 (dd, 1H); $^{13}$C NMR δ 13.6, 112.0, 116.1, 121.0, 124.7, 124.9, 133.0, 135.2, 140.1, 147.2, 150.0, 151.7.

Example 22

5-(2-Heptyl-benzoimidazol-1-yl)-pentanoic Acid tert-butyl Ester

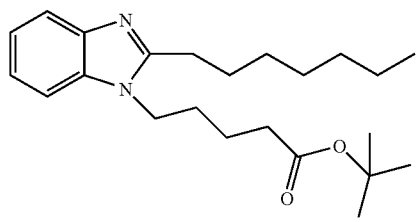

Method A applied to 1-iodo-2-nitrobenzene (125 mg, 0.5 mmol) and 5-octanoylamino-pentanoic acid tert-butyl ester (180 mg, 0.6 mmol) yielded the title compound as yellowy oil (40 mg, 38%). $^1$H NMR (DMSO) δ 0.86 (t, J=6.8Hz, 3H), 1.22-1.86 (m, 23H), 2.27 (t, J=7.3, 2H), 3.14 (t, J=7.8Hz, 2H), 4.43 (t, J=7.2Hz), 7.49-7.54 (m, 2H), 7.77 (d, J=8.8Hz, 1H), 7.93 (d, J=8.8Hz).

Example 23

6-(2-Methyl-benzoimidazol-1-yl)-hexanoic Acid Methyl Ester

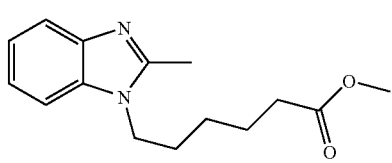

Method A applied to 1-iodo-2-nitrobenzene (125 mg, 0.5 mmol) and 6-acetylamino-hexanoic acid methyl ester (112 mg, 0.6 mmol) yielded the title compound as yellow oil (20 mg, 15%). $^1$H NMR (DMSO) δ 1.32-1.83 (m, 6H), 2.29 (t, J=7.1Hz, 2H), 2.80 (s, 3H), 3.55 (s, 3H), 4.38 (t, J=7.3, 2H), 7.48-7.56 (m, 2H), 7.76 (d, J=8.1Hz, 1H), 7.91 (d, J=8.1Hz).

Example 24

2-Cyclopentylmethyl-1-(2-methyl-butyl)-1H-benzimidazole-5-carboxylic Acid Methyl Ester

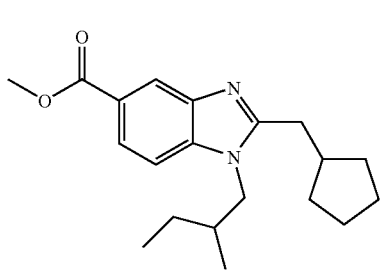

Method A applied to 1-iodo-2-nitrobenzene (125 mg, 0.5 mmol) and 2-cyclopentyl-N-(2-me-thyl-butyl)-acetamide (118 mg, 0.6 mmol) yielded the title compound as yellow oil (66 mg, 40%). $^1$H NMR (DMSO) δ 0.82 (d, 3H), 0.88 (t, 3H), 1.19-2.52 (m, 14H), 3.06 (d, 2H), 3.87 (s, 3H), 4.13 (dd, 1H), 4.24 (dd, 1H), 7.83 (d, 1H), 7.94 (d, 1H), 8.20 (s, 1H).

Example 25

2-Methyl-1-phenyl-1H-imidazo[4,5-c]pyridine

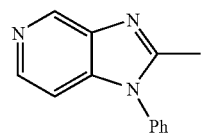

Method A applied to 4-chloro-3-nitropyridine (79 mg, 0.5 mmol), N-phenylacetamide (81 mg, 0.6 mmol) afforded the title compound as brown solid (76 mg, 73). mp 134-136° C. $^1$H NMR (DMSO) δ 2.54 (s, 3H), 7.65-7.73 (m, 6H), 8.54 (d, J=5.2Hz, 1H), 9.44 (s, 1H); $^{13}$C NMR δ 14.4, 108.2, 126.9, 130.2, 130.3, 133.4, 134.0, 134.8, 139.2, 145.0, 159.2. HRMS (FAB): cal. for $C_{13}H_{12}N_3$ [M+H$^+$]: 210.1031; found: 210.1025.

Example 26

2-Methyl-1-phenyl-1H-imidazo[4,5-b]pyridine

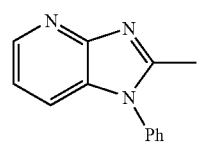

Method A applied to 3-chloro-2-nitropyridine (79 mg) and N-phenylacetamide (81 mg, 0.6 mmol) afforded the title compound as brown viscous oil (45 mg, 43% yield). $^1$H NMR (DMSO) δ 2.54 (s, 3H), 7.35-7.68 (m, 6H), 7.77 (d, J=8.8Hz, 1H), 8.58 (br s, 1H); $^{13}$C NMR δ 14.0, 118.9, 120.1, 126.8, 128.5, 129.6, 130.1, 133.9, 143.0, 151.6, 156.7. HRMS (FAB): cal. for $C_{13}H_{12}N_3$ [M+H$^+$]: 210.1031; found: 210.1026.

Example 27

2-Methyl-3-phenyl-3H-imidazo[4,5-b]pyridine

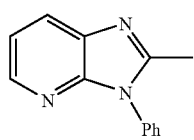

Method A applied to 2-chloro-3-nitropyridine (79 mg, 0.5 mmol) and N-phenylacetamide (81 mg, 0.6 mmol) afforded the title compound as pale yellow viscous oil (93 mg, 89%). $^1$H NMR (DMSO) δ 2.48 (s, 3H), 7.24 (dd, 1H), 7.53-7.63 (m, 5H), 8.02 (d, 1H), 8.20 (d, 1H); $^{13}$C NMR δ 14.6, 118.3, 125.9, 127.4, 128.7, 129.3, 134.1, 134.3, 143.0, 148.7, 152.9. HRMS (FAB): cal. for $C_{13}H_{12}N_3$ [M+H$^+$]: 210.1031; found: 210.1027.

Example 28

2,6-Dimethyl-3-phenyl-3H-imidazo[4,5-b]pyridine

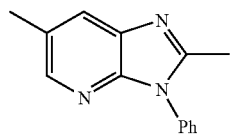

Method A applied to 2-chloro-5-methyl-3-nitropyridine (86 mg, 0.5 mmol) and N-phenylacetamide (81 mg, 0.6 mmol) afforded the title compound as brown solid (90 mg, 81%). mp 77-79° C. $^1$H NMR (DMSO) δ 2.44 (s, 3H), 2.54 (s, 3H), 7.56-7.63 (m, 5H), 7.95 (s, 1H), 8.20 (s, 1H); $^{13}$C NMR δ 13.1, 17.9, 124.4, 127.5, 129.5, 129.6, 129.8, 132.9, 145.1, 145.7, 153.2. HRMS (FAB): cal. for $C_{14}H_{14}N_3$ [M+H$^+$]: 224.1187; found: 224.1184.

Example 29

5-Methoxy-2-methyl-3-phenyl-3H-imidazo[4,5-b]pyridine

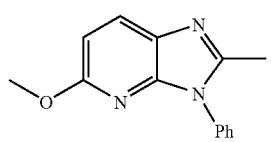

Method A applied to 2-chloro-6-methoxy-3-nitropyridine (94 mg, 0.5 mmol) and N-phenylacetamide (81 mg, 0.6 mmol) afforded the title compound as pale yellow solid (112 mg, 94%). mp 114-116° C. $^1$H NMR (DMSO) δ 2.56 (s, 3H), 3.76 (s, 3H), 6.85 (d, J=8.6Hz, 1H), 7.53-7.68 (m, 5H), 8.12 (d, J=8.6Hz, 1H). $^{13}$C NMR δ 13.8, 53.4, 107.7, 122.9, 127.0, 128.0, 128.4, 129.2, 132.6, 144.1, 150.3, 161.1. HRMS (FAB): cal. for $C_{14}H_{14}N_3O$ [M+H$^+$]: 240.1237; found: 240.1234.

Example 30

2,5-Dimethyl-3-phenyl-3H-imidazo[4,5-b]pyridine

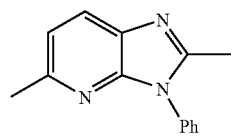

Method A applied to 2-chloro-6-methyl-3-nitropyridine (86 mg, 0.5 mmol) and N-phenylacetamide (81 mg, 0.6 mmol) afforded the title compound as brown viscous oil (70 mg, 63%). $^1$H NMR (DMSO) δ 2.42 (s, 3H), 3.31 (s, 3H), 7.11 (d, J=8.0Hz, 1H), 7.51-7.63 (m, 5H), 7.89 (d, J=8.0Hz, 1H); $^{13}$C NMR δ 14.6, 23.8, 118.0, 126.1, 127.7, 128.7, 129.4, 132.1, 134.8, 148.3, 150.9, 151.1. HRMS: cal. for $C_{14}H_{14}N_3$ [M+H$^+$]: 224.1188; found: 224.1184.

Example 31

2,7-Dimethyl-3-phenyl-3H-imidazo[4,5-b]pyridine

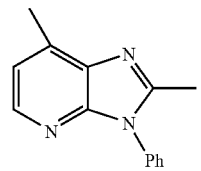

Method A applied to 2-chloro-4-methyl-3-nitropyridine (86 mg, 0.5 mmol) and N-phenylacetamide (81 mg, 0.6 mmol) afforded the title compound as pale yellow solid (70 mg, 63%). mp 117-119° C. $^1$H NMR (DMSO) δ 2.59 (s, 3H), 2.73 (s, 3H), 7.26 (d, J=4.8Hz, 1H), 7.58-7.72 (m, 5H), 8.22 (d, J=4.8Hz, 1H); $^{13}$C NMR δ 13.8, 16.0, 120.8, 127.3, 129.3, 129.4, 129.5, 130.1, 136.0, 144.2, 146.4, 152.1. HRMS (FAB): cal. for $C_{14}H_{14}N_3$ [M+H$^+$]: 224.1188; found: 224.1180.

Example 32

5-Methoxy-3-phenyl-2-pyridin-3-yl-3H-imidazo[4,5-b]pyridine

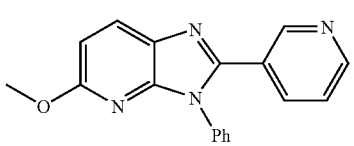

Method B applied to 2-chloro-6-methoxy-3-nitro-pyridine (94 mg, 0.5 mmol) and N-pyridin-3-ylacetamide (82 mg, 0.6 mmol) afforded the title compound as viscous oil (74 mg, 49%). $^1$H NMR (DMSO) δ 3.79 (s, 3H), 6.83 (d, J=8.1Hz, 1H), 7.44-7.83 (m, 7H), 8.14 (d, J=8.1Hz, 1H), 8.57 (d, J=8.1Hz, 1H), 8.68 (s, 1H).

Example 33

5-(5-Methyl-3-phenyl-3H-imidazo[4,5-b]pyridin-2-yl)-pentanoic Acid Methyl Ester

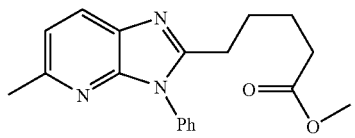

Method B applied to 2-chloro-6-methyl-3-nitropyridine (86 mg, 0.5 mmol) and 5-phenylcarbamoyl-pentanoic acid methyl ester (141 mg, 0.6 mmol) afforded the title compound as viscous oil (61 mg, 38%). $^1$H NMR (DMSO) δ 1.52-1.73 (m, 4H), 2.22 (t, J=6.8Hz, 2H), 2.48 (s, 3H), 2.75 (t, J=6.8Hz, 2H), 3.53 (s, 3H), 7.13 (d, J=8.0 Hz), 7.47-7.63 (m, 5H), 7.93 (d, J=8.0Hz).

Example 34

2,6-Dimethyl-3-phenethyl-3H-imidazo[4,5-b]pyridine

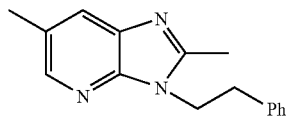

Method B applied to 2-chloro-5-methyl-3-nitropyridine (86 mg, 0.5 mmol) and N-phenethyl-acetamide (98 mg, 0.6 mmol) afforded the title compound as viscous oil (54 mg, 43%). $^1$H NMR (DMSO) δ 2.38 (s, 3H), 2.46 (s, 3H), 3.12 (t, 2H), 4.53 (t, 2H), 7.08-7.29 (m, 5H), 7.93 (s, 1H), 8.32 (s, 1H).

Example 35

1-Phenyl-2-tridecyl-1H-imidazo[4,5-c]pyridine

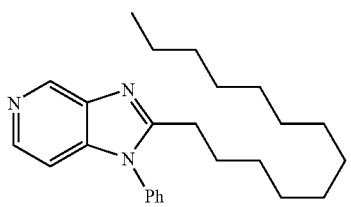

Method B applied to 4-chloro-3-nitropyridine (79 mg, 0.5 mmol) and tetradecanoic acid phenylamide (182 mg, 0.6 mmol) afforded the title compound as viscous oil (64 mg, 34%). $^1$H NMR (DMSO) δ 0.83 (t, J=6.7Hz, 3H), 1.16-1.32 (m, 20H), 1.73 (p, J=6.7 Hz, 2H), 2.83 (t, J=6.7Hz, 2H). 7.63-7.71 (m, 6H), 8.56 (d, J=5.2Hz, 1H), 9.43 (s, 1H).

Example 36

4-(2,6-Dimethylimidazo[4,5-b]pyridin-3-yl)-2-ethoxybenzoic acid methyl ester

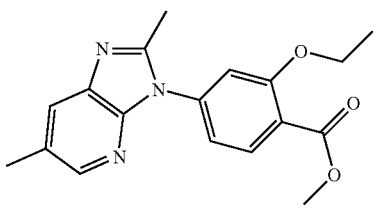

Method B applied to 2-chloro-5-methyl-3-nitropyridine (86 mg, 0.5 mmol) and 4-acetylamino-2-ethoxybenzoic acid methyl ester (142 mg, 0.6 mmol) afforded the title compound as viscous oil (136 mg, 84%). $^1$H NMR (DMSO) δ 1.34 (t, J=6.9Hz, 3H), 2.46 (s, 3H), 2.61 (s, 3H), 3.82 (s, 3H), 4.12 (q, J=6.9Hz, 2H), 7.22 (d, J=8.0Hz, 1H), 7.50 (s, 1H), 7.83 (d, J=8.0Hz, 1H), 7.98 (s, 1H), 8.21 (s, 1H).

Example 37

5-Methoxy-2-methyl-3-pyridin-2-yl-3H-imidazo[4,5-b]pyridine

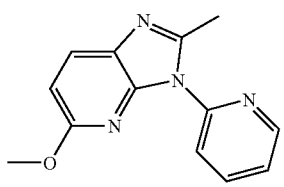

Method B applied to 2-chloro-6-methoxy-3-nitropyridine (94 mg, 0.5 mmol) and N-pyridin-2-ylacetamide (82 mg, 0.6 mmol) afforded the title compound as viscous oil (32 mg, 27%). $^1$H NMR (DMSO) δ 2.66 (s, 3H), 3.82 (s, 3H), 6.81 (d, J=8.5Hz, 1H), 7.58 (dd, J=7.6, 4.7Hz, 1H), 7.95 (d, J=7.9Hz, 1H), 8.04 (d, J=8.5Hz, 1H), 8.14 (dd, J=7.9, 7.6Hz, 1H), 8.69 (d, J=4.7Hz, 1H).

Example 38

2-(5-Chloro-pentyl)-5-methoxy-3-phenyl-3H-imidazo[4,5-b]pyridine

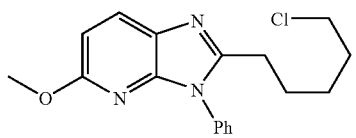

Method B applied to 2-chloro-6-methoxy-3-nitropyridine (94 mg, 0.5 mmol) and 6-chlorohexanoic acid phenylamide (113 mg, 0.6 mmol) afforded the title compound as viscous oil (94 mg, 57%). ¹H NMR (DMSO) δ 1.34-1.41 (m, 2H), 1.62-1.71 (m, 6H), 2.78 (t, J=6.8Hz, 2H), 3.73 (s, 3H), 6.73 (d, J=8.6Hz, 1H), 7.53-7.63 (m, 5H), 7.98 (d, J=8.6Hz, 1H).

Example 39

1-(4-Methoxyphenyl)-2-methyl-1H-imidazo[4,5-c]pyridine

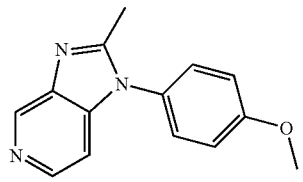

Method B applied to 4-chloro-3-nitropyridine (79 mg, 0.5 mmol) and N-(4-methoxyphenyl)acetamide (99 mg, 0.6 mmol) afforded the title compound as viscous oil (84 mg, 70%). ¹H NMR (DMSO) δ 2.55 (s, 3H), 3.88 (s, 3H), 7.21 (d, J=8.8Hz, 2H), 7.57 (d, J=8.8Hz, 2H), 7.69 (d, J=5.4Hz, 1H), 8.57 (d, J=5.4Hz, 1H), 9.44 (s, 1H).

What is claimed is:

1. A process for preparing a compound of formula I

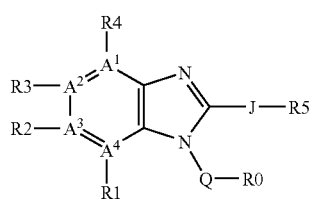

or a stereoisomeric form of the compound of formula I, or a mixture of these forms in any ratio, or a physiologically tolerated salt of a compound of formula I, wherein A1, A2, A3, A4 are each carbon to form together with the two carbon atoms in formula I a stable aromatic ring;

Q is —($C_1$-$C_6$)-alkylene, wherein the alkylene is unsubstituted or mono-, di- or trisubstituted independently of one another by R14;

—($C_3$-$C_8$)-cycloalkyl, wherein the cycloalkyl is unsubstituted or mono-, di- or trisubstituted independently of one another by R14;

—($C_6$-$C_{14}$)-aryl, wherein the aryl is unsubstituted or mono-, di-, tri- or four times substituted independently of one another by R13; or —($C_4$-$C_{14}$)-heteroaryl, wherein the heteroaryl is unsubstituted or mono-, di-, tri- or four times substituted independently of one another by R13;

J is —($C_1$-$C_6$)-alkylene, wherein the alkylene is unsubstituted or mono-, di- or trisubstituted independently of one another by R14;

—($C_3$-$C_8$)-cycloalkyl, wherein the cycloalkyl is unsubstituted or mono-, di- or trisubstituted independently of one another by R14;

—($C_6$-$C_{14}$)-aryl, wherein the aryl is unsubstituted or mono-, di-, tri- or four times substituted independently of one another by R13; or —($C_4$-$C_{14}$)-heteroaryl, wherein the heteroaryl is unsubstituted or mono-, di-, tri- or four times substituted independently of one another by R13;

R0, R1, R2, R3, R4 and R5 are independent of one another identical or different and are
 a) hydrogen atom,
 b) —($C_1$-$C_4$)-alkyl, wherein the alkyl is unsubstituted or substituted one to three times by R13,
 c) halogen,
 d) phenyloxy-, wherein the phenyloxy is unsubstituted or substituted one to three times by R13,
 e) —($C_1$-$C_3$)-fluoroalkyl,
 f) —N(R10)-($C_1$-$C_4$)-alkyl, wherein the alkyl is unsubstituted or substituted one to three times by R13,
 g) —($C_6$-$C_{14}$)-aryl, wherein the aryl is unsubstituted or mono-, di-, tri- or four times substituted independently of one another by R13,
 h) —($C_4$-$C_{14}$)-heteroaryl, wherein the heteroaryl is unsubstituted or mono-, di-, tri- or four times substituted independently of one another by R13,
 i) —($C_3$-$C_8$)-cycloalkyl, wherein the cycloalkyl is unsubstituted or mono-, di-, tri- or four times substituted independently of one another by R13, or
 j) a 3- to 7-membered cyclic residue, containing up to 1, 2, 3 or 4 heteroatoms chosen from nitrogen, sulfur or oxygen, wherein said cyclic residue is unsubstituted or mono-, di-, tri- or four times substituted independently of one another by R13,
 k) —O—$CF_3$,
 l) —O—($C_1$-$C_4$)-alkyl, wherein the alkyl is unsubstituted or substituted one to three times by R13,
 m) —$NO_2$,
 n) —CN,
 o) —OH,
 p) —C(O)—R10,
 q) —C(O)—O—R11,
 r) —C(O)—N(R11)-R12,
 s) —N(R11)-R12,
 t) —N(R10)-$SO_2$—R10,
 v) —S—R10,
 w) —$SO_1$R10, wherein n is 1 or 2,
 x) —$SO_2$—N(R11)(R12) or
 y) at least one of R1, R2, R3 or R4 are absent in case one or more of A1, A2, A3 or A4 is a nitrogen atom, or R1 and R2, R2 and R3 or R3 and R4 form together with the atoms which they are attached to a 5- or 8-membered ring, containing 0, 1, 2, 3 or 4 heteroatoms chosen from nitrogen, sulfur or oxygen, wherein said ring is unsubstituted or substituted one, two, three or four times by R14, R10 is hydrogen atom, —($C_1$-$C_3$)-fluoroalkyl or —($C_1$-$C_6$)-alkyl, R11 and R12 are independently of one another identical or different and are
 a) hydrogen atom,
 b) —($C_1$-$C_6$)-alkyl, wherein the alkyl is unsubstituted or mono-, di- or trisubstituted independently of one another by R13,
 c) —($C_6$-$C_{14}$)-aryl-, wherein the aryl is unsubstituted or mono-, di- or trisubstituted independently of one another by R13,
 d) —($C_4$-$C_{14}$)-heteroaryl, wherein the heteroaryl is unsubstituted or mono-, di- or trisubstituted independently of one another by R13 or R13 is halogen, —NO₂, —CN, =O, —OH, —(C₁-C₈)-alkyl, —(C₁-C₈)-alkoxy,
—CF₃, phenyloxy-, —C(O)—O—R17, —C(O)—N—(R17)-R18, —N(R17)-R18, —C(O)—R10,
—N(R10)-SO₂—R10, —S—R10, —SOₙ—R10, wherein n is 1 or 2, —SO₂—N(R17)-R18,
—(C₆-C₁₄)-aryl, wherein the aryl is unsubstituted or mono-, di- or trisubstituted independently of one another by R14, —(C₄-C₁₄)-heteroaryl, wherein the heteroaryl is unsubstituted or mono-, di- or trisubstituted independently of one another by R14, —(C₃-C₈)-cycloalkyl, wherein the cycloalkyl is unsubstituted or mono-, di- or trisubstituted independently of one another by R14, or a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, R14 is halogen, —OH, =O, —CN, —CF₃, —(C₁-C₈)-alkyl, —(C₁-C₄)-alkoxy,
—NO₂, —C(O)—OH, —NH₂, —C(O)—O—(C₁-C₄)-alkyl, —(C₁-C₈)-alkylsulfonyl,
—C(O)—NH—(C₁-C₈)-alkyl, —C(O)—N[(C₁-C₈)-alkyl]₂, —C(O)—NH₂, —S—R10,
—N(R10)-C(O)—NH—(C₁-C₈)-alkyl, or —N(R10)-C(O)—N[(C₁-C₈)-alkyl]₂, R17 and R18 are independently of one another identical or different and are
 a) hydrogen atom,
 b) —(C₁-C₆)-alkyl,
 c) —(C₆-C₁₄)-aryl- or
 d) —(C₄-C₁₄)-heteroaryl, said process comprising reacting a compound of formula II

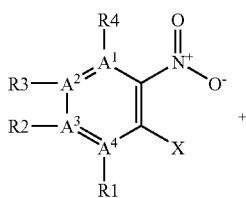

(II)

wherein R1, R2, R3, R4, A1, A2, A3 and A4 are as defined in formula I and
X is Cl, Br, I, triflate or nonaflate, with a compound of formula III

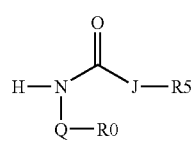

(III)

wherein Q, J, R0 and R5 are as defined in formula I,
in the presence of a palladium catalyst, a base, a ligand and an aprotic solvent to give a compound of formula IV

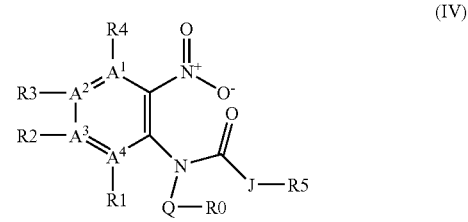

(IV)

and converting the compound of formula IV into a compound of formula I in the presence of a reducing reagent and a second solvent, and
optionally converting the compound of formula I to a physiologically tolerated salt thereof.

2. The process according to claim 1, wherein a compound of formula I is prepared, wherein
 A1, A2, A3 and A4 form together with the two carbon atoms in formula I a benzene,
 Q is —(C₁-C₆)-alkylene, wherein the alkylene is unsubstituted or mono-, di- or trisubstituted independently of one another by R14;
 —(C₃-C₆)-cycloalkyl, wherein the cycloalkyl is unsubstituted or mono-, di- or trisubstituted independently of one another by R14;
 phenyl, wherein the phenyl is unsubstituted or mono-, di-, tri- or four times substituted independently of one another by R13; or
 —(C₄-C₁₄)-heteroaryl, wherein the heteroaryl is selected from acridinyl, azaindole (1H-pyrrolopyridinyl), azabenzimidazolyl, azaspirodecanyl, azepinyl, azetidinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, imidazolyl, indanyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxathiepanyl, 1,2-oxathiolanyl, 1,4-oxazepanyl, 1,4-oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl, and wherein the heteroaryl is unsubstituted or mono-, di-, tri- or four times substituted independently of one another by R13;

J is

—$(C_1-C_6)$-alkylene, wherein the alkylene is unsubstituted or mono-, di- or trisubstituted independently of one another by R14;

—$(C_3-C_6)$-cycloalkyl, wherein the cycloalkyl is unsubstituted or mono-, di- or trisubstituted independently of one another by R14;

phenyl, wherein the phenyl is unsubstituted or mono-, di-, tri- or four times substituted independently of one another by R13; or —$(C_4-C_{14})$-heteroaryl, wherein the heteroaryl is unsubstituted or mono-, di-, tri- or four times substituted independently of one another by R13;

R0, R1, R2, R3, R4 and R5 are independent of one another identical or different and are a) hydrogen atom,
b) F,
c) Cl or Br,
d) —$(C_1-C_4)$-alkyl, wherein the alkyl is unsubstituted or substituted one to three times by R13,
e) —$(C_1-C_3)$-fluoroalkyl,
f) phenyl, wherein the phenyl is unsubstituted or substituted one to three times by R13,
g) —$(C_4-C_{14})$-heteroaryl, wherein the heteroaryl is unsubstituted or mono-, di-, tri- or four times substituted independently of one another by R13,
h) —$(C_3-C_8)$-cycloalkyl, wherein the cycloalkyl is unsubstituted or mono-, di-, tri- or four times substituted independently of one another by R13,
i) a 3- to 7-membered cyclic residue selected from azepine, azetidine, aziridine, azirine, 1,4 diazepane, 1,2-diazepine, 1,3-diazepine, 1,4-diazepine, diaziridine, diazirine, dioxazine, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, and is unsubstituted or mono-, di-, tri- or four times substituted independently of one another by R13,
j) —O—$CF_3$,
k) —O—$(C_1-C_4)$-alkyl, wherein the alkyl is unsubstituted or substituted one to three times by R13,
l) —N(R10)-$(C_1-C_4)$-alkyl, wherein the alkyl is unsubstituted or substituted one to three times by R13,
m) —CN,
n) —OH,
o) phenyloxy-, wherein the phenyloxy is unsubstituted or substituted one to three times by R13,
p) —C(O)—O—R11,
q) —C(O)—N(R11)-R12,
r) —N(R11)-R12,
s) —N(R10)-$SO_2$—R10,
t) —S—R10,
v) —$SO_n$—R10, wherein n is 1 or 2,
w) —$SO_2$—N(R11)-R12,
x) —C(O)—R10 or
y) at least one of R1, R2, R3 or R4 are absent in case one or more of A1, A2, A3 or A4 is a nitrogen atom, R10 is hydrogen atom, —$(C_1-C_3)$-fluoroalkyl or —$(C_1-C_6)$-alkyl, R11 and R12 are independently of one another identical or different and are a) hydrogen atom,
b) —$(C_1-C_4)$-alkyl, wherein the alkyl is unsubstituted or mono-, di- or trisubstituted independently of one another by R13,
c) phenyl, wherein the phenyl is unsubstituted or mono-, di- or trisubstituted independently of one another by R13,
d) —$(C_4-C_{14})$-heteroaryl, wherein the heteroaryl is unsubstituted or mono-, di- or trisubstituted independently of one another by R13 or R13 is F, Cl, —CN, =O, —OH, —$(C_1-C_8)$-alkyl, —$(C_1-C_8)$-alkoxy, —$CF_3$, phenyloxy-, —C(O)—R10, —C(O)—O—R17, —C(O)—N(R17)-R18, —N(R17)-R18, —N(R10)-$SO_2$—R10, —S—R10, —$SO_n$—R10, wherein n is 1 or 2, —$SO_2$—N(R17)-R18, phenyl, wherein the phenyl is unsubstituted or mono-, di- or trisubstituted independently of one another by R14, —$(C_4-C_{14})$-heteroaryl, wherein the heteroaryl is unsubstituted or mono-, di- or trisubstituted independently of one another by R14, —$(C_3-C_6)$-cycloalkyl, wherein said cycloalkyl is unsubstituted or mono-, di- or trisubstituted independently of one another by R14, or a 3- to 7-membered cyclic residue, containing up to 1, 2, 3 or 4 heteroatoms chosen from nitrogen, sulfur or oxygen, which is unsubstituted or mono-, di- or trisubstituted independently of one another by R14, R14 is F, Cl, —OH, =O, —CN, —$CF_3$, —$(C_1-C_8)$-alkyl, —$(C_1-C_4)$-alkoxy, —C(O)—OH, —$NH_2$, —C(O)—O—$(C_1-C_4)$-alkyl, —$(C_1-C_8)$-alkylsulfonyl, —C(O)—$NH_2$, —S—R10, —C(O)—NH—$(C_1-C_8)$-alkyl, —C(O)—N[$(C_1-C_8)$-alkyl]$_2$, —N(R10)-C(O)—NH—$(C_1-C_8)$-alkyl or —N(R10)-C(O)—N[$(C_1-C_8)$-alkyl]$_2$, R17 and R18 are independently of one another identical or different and are a) hydrogen atom,
b) —$(C_1-C_4)$-alkyl,
c) phenyl or
d) —$(C_4-C_{14})$-heteroaryl and X is Cl, Br or I.

3. The process according to claim 1, wherein a compound of formula I is prepared, wherein A1, A2, A3 and A4 form together with the two carbon atoms in formula I a benzene, Q is phenyl, which is unsubstituted or substituted by R13, —$(C_1-C_6)$-alkylene or pyridyl, R0, R1, R2, R3, R4 and R5 are independent of one another identical or different and are a) hydrogen atom,
b) F, c) Cl,
d) Br,
e) —($C_1$-$C_4$)-alkyl,
f) —($C_3$-$C_6$)-cycloalkyl
g) phenyl,
h) —O—($C_1$-$C_4$)-alkyl,
i) —C(O)—O—R11,
j) —CN,
k) —C(O)—R10 or
l) at least one of R1, R2, R3 or R4 are absent in case one or more of A1, A2, A3 or A4 is a nitrogen atom,
R10 is hydrogen atom or —($C_1$-$C_4$)-alkyl,
R11 is hydrogen atom or —($C_1$-$C_4$)-alkyl,
R13 is —C(O)—O—R17,
R14 is Cl, F, —($C_1$-$C_8$)-alkyl or —C(O)—O—($C_1$-$C_4$)-alkyl,
R17 is hydrogen atom or —($C_1$-$C_4$)-alkyl and
X is Cl, Br or I.

4. The process according to claim 1, wherein one of the following compounds of formula I is prepared:
5-Chloro-2-methyl-1-phenyl-1H-benzimidazole;
2-Methyl-1-phenyl-1H-benzimidazole;
7-Chloro-2-methyl-1-phenyl-1H-benzimidazole;
2,7-Dimethyl-1-phenyl-1H-benzimidazole;
5-Methoxy-2-methyl-1-phenyl-1H-benzimidazole;
2-Methyl-1-phenyl-1H-benzimidazole-5-carbaldehyde;
1,2-Diphenyl-1H-benzimidazole;
1-Phenyl-2-pyridin-3-yl-1H-benzimidazole;
1-Phenyl-2-tridecyl-1H-benzimidazole;
1,2-dimethyl-1H-benzimidazole;
2-Methyl-1-phenethyl-1H-benzimidazole;
2-Methyl-1-pyridin-2-yl-1H-benzimidazole;
5-(1-Phenyl-1H-benzoimidazol-2-yl)-pentanoic acid methyl ester;
2-(5-Chloro-pentyl)-1-phenyl-1H-benzimidazole;
1-(4-Methoxy-phenyl)-2-methyl-1H-benzimidazole;
4-(2-Methyl-benzoimidazol-1-yl)-benzonitrile;
2-Ethoxy-4-(2-methyl-benzoimidazol-1-yl)-benzoic acid methyl ester,
2,4-Dimethyl-1-phenyl-1H-benzimidazole;
5-cyano-2-methyl-1-phenyl-1H-benzimidazole;
2-Methyl-1-pyridin-2-yl-1H-benzimidazole;
5-(2-Heptyl-benzoimidazol-1-yl)-pentanoic acid tert-butyl ester;
6-(2-Methyl-benzoimidazol-1-yl)-hexanoic acid methyl ester; or
2-Cyclopentylmethyl-1-(2-methyl-butyl)-1H-benzimidazole-5-carboxylic acid methyl ester.

5. The process according to claim 1, wherein the palladium catalyst is selected from the group consisting of Pd-alkanoates, Pd-alkanoate complexes, Pd-acetonates, Pd-halides, Pd-halide complexes and Pd-phosphine complexes.

6. The process according to claim 5, wherein the palladium catalyst is selected from the group consisting of palladium (II) acetate, palladium (II) trifluoroacetate, tris(dibenzylidene-acetone)dipalladium(0), tris(dibenzylideneacetone)dipalladium(0) chloroform adduct, palladium (II) chloride, 2,2'-bis(diphenylphosphino)-1,1'-binaphthylpalladium (II) chloride, acetato(2'-di-tert-butylphosphino-1,1'-biphenyl-2-yl)palladium(II), (1,2-Bis(diphenylphosphino)ethane)dichloropalladium(II), Bis[1,2-bis(diphenylphosphino)ethane]palladium (0), [(2S,3S)-Bis(diphenyl-phosphino)butane] [eta3-allyl]palladium(II) perchlorate, and 1,3-bis(2,4,6-trimethylphenyl)imidazol-2-ylidene(1,4-naphthoquinone)palladium (0) dimer.

7. The process according to claim 5, wherein the palladium catalyst is palladium (II) acetate, 2,2'-bis(diphenylphosphino)-1,1'-binaphthylpalladium(II) chloride or palladium (II) trifluoroacetate.

8. The process according to claim 1, wherein the base is selected from the group consisting of carbonates, phosphates, fluorides, alkoxides and hydroxides with a metal as counterion.

9. The process according to claim 8, wherein the base is selected from the group consisting of potassium carbonate, potassium phosphate and cesium carbonate.

10. The process according to claim 1, wherein the ligand is selected from the group consisting of (+/−)-2,2'-bis(diphenylphosphino)-1,1'-binaphthalene, 4,5-Bis(diphenyl-phosphino)-9,9-dimethylxanthene, (R)-(−)-1-[(5)-2-(diphenylphosphino) ferrocenyl]ethyldicyclohexylphosphine, 1,2-Bis(diphenylphosphino)ethane, 1,3-Bis(diphenylphosphino) propane, (R)-(−)-1-[(S)-2-(Dicyclohexylphosphino)-ferrocenyl]ethyldi-tert-butylphosphine, (R)-(+)-1,1'-Bis(diphenylphosphino)-2,2'-bis(N,N-diiisopropylamido) ferrocene, (S,S)-1-[1-(Di-tert-butylphosphino)ethyl]-2-(diphenylphosphino)ferrocene, (1R,2R)-(+)-1,2-Diaminocyclohexane-N,N'-bis(2-diphenylphosphino-1-naphtoyl, (−)-1,2-Bis((2S,5S)-2,5-diisopropylphospholano)-benzene, Bis[(2-diphenylphosphino) phenyl]ether, (5)-(+2,T-Bis(di-para-tolylphosphino)-1,1'-binaphyl, 4,5-Bis(bis(3,5-bis(trifluoromethyl)phenyl)-phosphino)-9,9-dimethylxanthen, 2,2'-bis[(2',4',6'-triisopropyl)dicyclohexyl-phosphino]biphenyl and 2,2'-bis(di-tert-butylphosphino)biphenyl, tri-tert-butylphosphine.

11. The process according to claim 10, wherein the ligand is 2,2'-bis(diphenyl-phosphino)-1,1'-binaphthalene or 4,5-Bis(diphenylphosphino)-9,9-dimethylxanthene.

12. The process according to claim 1, wherein the aprotic solvent is selected from the group consisting of benzene, toluene, xylene, mesitylene, acetonitrile, tetrahydrofuran, dimethylformamide, n-methylpyrrolidinone, dimethylacetamide, dimethylsulfoxide, (2-methoxyethyl)ether and pyridine.

13. The process according to claim 12, wherein the aprotic solvent is selected from the group consisting of benzene, mesitylene and toluene.

14. The process according to claim 1, wherein the reaction between the compound of formula II and formula III is carried out at a temperature in the range of 60° C. to 150° C.

15. The process according to claim 14, wherein said temperature is the range of 70° C. to 90° C.

16. The process according to claim 1, wherein the second solvent is selected from the group consisting of methanol, ethanol, propanol, acetic acid, methylene chloride, dimethylformamide, tetrahydrofuran, pyridine, p-xylene, ethylacetate, benzene, toluene, xylene, mesitylene and acetonitrile.

17. The process according to claim 16, wherein the second solvent is selected from the group consisting of methanol, ethanol, acetic acid, methylene chloride, dimethylformamide, pyridine and p-xylene.

18. The process according to claim 1, wherein the reducing reagent is selected from the group consisting of $H_2$/Raney-$N_1$, $H_2$/Pd—C, $H_2$/$PtO_2$, $H_2$/Ru, $NaBH_4$/$NiCl_2$, $NaBH_4$/$FeCl_2$, $H_3PO_2$/Pd—C, Sn/HCl, $SnCl_2$/HCl, Fe/HOAc, Fe/HCl, $FeSO_4$/HCl, Fe/$FeSO_4$, Zn/HCl, $Na_2S$, and $Na_2S_2O_4$.

19. The process according to claim 1, wherein the reduction reaction of the compound of formula IV to the compound of formula I is carried out at a temperature in the range of 80° C. to 140° C.

20. The process according to claim 19, wherein said temperature is in the range of 110° C. to 120° C.

* * * * *